US 10,900,013 B2
Jan. 26, 2021

(12) United States Patent
Krivov

(10) Patent No.: US 10,900,013 B2
(45) Date of Patent: Jan. 26, 2021

(54) SYSTEMS AND METHODS OF PRODUCING COMPOSITIONS FROM THE NUTRIENTS RECOVERED FROM WASTE STREAMS

(71) Applicant: GSR Solutions LLC, Burlington, VT (US)

(72) Inventor: Anju D. Krivov, Burlington, VT (US)

(73) Assignee: GSR Solutions, LLC, Burlington, VT (US)

(*) Notice: Subject to any disclaimer, the term of this patent is extended or adjusted under 35 U.S.C. 154(b) by 335 days.

(21) Appl. No.: 15/856,642

(22) Filed: Dec. 28, 2017

(65) Prior Publication Data
US 2018/0119085 A1    May 3, 2018

Related U.S. Application Data

(63) Continuation-in-part of application No. 14/932,218, filed on Nov. 4, 2015, now abandoned, which is a
(Continued)

(51) Int. Cl.
*C02F 11/02*    (2006.01)
*C02F 11/04*    (2006.01)
(Continued)

(52) U.S. Cl.
CPC ............. *C12M 43/00* (2013.01); *C02F 3/322* (2013.01); *C02F 3/325* (2013.01); *C02F 11/02* (2013.01);
(Continued)

(58) Field of Classification Search
None
See application file for complete search history.

(56) References Cited

U.S. PATENT DOCUMENTS 5,985,147 A * 11/1999 Jensen ................. C02F 3/32
                                      162/218
6,350,350 B1 * 2/2002 Jensen ................. C05F 11/00
                                      162/141
(Continued)

FOREIGN PATENT DOCUMENTS

WO    1993-24418      12/1993
WO    2003-065798 A1    8/2003
(Continued)

OTHER PUBLICATIONS

Schonwasser, "Supplementary European Search Report", related to European Application No. 15852804.2, dated Oct. 5, 2018.
(Continued)

*Primary Examiner* — Wayne A Langel
(74) *Attorney, Agent, or Firm* — Shawn Gordon, Esq.; Dunkiel Saunders Elliott Raubvogel & Hand, PLLC

(57) ABSTRACT

According to present disclosure, there is disclosed an algae growth and cultivation system that provides a cost-efficient means of producing algae biomass as feedstock for algae-based products, such as, fertilizer, feed, biofuel manufacture, and desirably impacts, nutrient recovery from waste streams for valued byproducts production, recycle water, and alternative/renewable energy production. The system as discussed herein is an integrated systems approach to wastewater treatment, algal strains selection for byproducts production, and recycle of algal biomass-processing waste or additional algae harvested as feedstock for products such as fertilizer production. Embodiments of a system as discussed herein present an economically viable algae production system and process that allows algae-derived products such as fertilizer, feed, biofuels, etc. to compete with non-organic or petroleum products in the marketplace.

13 Claims, 14 Drawing Sheets

Related U.S. Application Data continuation-in-part of application No. 14/888,986, filed as application No. PCT/US2015/056344 on Oct. 20, 2015, now abandoned.

(60) Provisional application No. 62/079,135, filed on Nov. 13, 2014, provisional application No. 62/067,042, filed on Oct. 22, 2014, provisional application No. 62/067,049, filed on Oct. 22, 2014.

(51) Int. Cl.
| | |
|---|---|
| *C05F 11/08* | (2006.01) |
| *C12M 1/00* | (2006.01) |
| *C02F 3/32* | (2006.01) |
| *C12M 1/107* | (2006.01) |
| *C02F 103/20* | (2006.01) |
| *C02F 103/32* | (2006.01) |

(52) U.S. Cl.
CPC ............ *C02F 11/04* (2013.01); *C05F 11/08* (2013.01); *C12M 1/002* (2013.01); *C12M 21/02* (2013.01); *C12M 21/04* (2013.01); *C12M 21/12* (2013.01); *C12M 29/18* (2013.01); *C12M 29/24* (2013.01); *C12M 45/00* (2013.01); *C12M 47/10* (2013.01); *C02F 2103/20* (2013.01); *C02F 2103/32* (2013.01); *C02F 2305/06* (2013.01); *Y02P 20/59* (2015.11)

(56) References Cited

U.S. PATENT DOCUMENTS

| | | | | |
|---|---|---|---|---|
| 6,423,229 B1* | 7/2002 | Mao | ........................ | C02F 3/286 |
| | | | | 210/603 |
| 7,850,848 B2* | 12/2010 | Limcaco | .................... | C10L 3/08 |
| | | | | 210/602 |
| 9,481,611 B2* | 11/2016 | Callendrello | ............. | C05C 9/00 |
| 2002/0056690 A1 | 5/2002 | Wegner | | |
| 2003/0201225 A1 | 10/2003 | Josse et al. | | |
| 2005/0023220 A1 | 2/2005 | Barak et al. | | |
| 2007/0105205 A1* | 5/2007 | Jarventie | .................... | C05C 3/00 |
| | | | | 435/161 |
| 2007/0142693 A1 | 6/2007 | Adachi et al. | | |
| 2008/0135475 A1* | 6/2008 | Limcaco | ................. | C02F 3/082 |
| | | | | 210/602 |
| 2009/0324799 A1* | 12/2009 | Hartman | .................... | C05F 7/00 |
| | | | | 426/635 |
| 2010/0255562 A1* | 10/2010 | Kang | ........................ | C02F 9/00 |
| | | | | 435/262 |
| 2011/0294175 A1 | 12/2011 | Bellussi et al. | | |
| 2012/0024780 A1* | 2/2012 | Carr | ........................ | C05F 11/00 |
| | | | | 210/602 |
| 2014/0199759 A1 | 7/2014 | Van Alstyne et al. | | |
| 2014/0223981 A1* | 8/2014 | Hatcher | .................. | C05C 11/00 |
| | | | | 71/23 |
| 2015/0128838 A1* | 5/2015 | Bryan | ..................... | C12M 33/00 |
| | | | | 114/61.1 |
| 2016/0115432 A1 | 4/2016 | Dahiya | | |
| 2016/0122705 A1* | 5/2016 | Lancaster | .............. | C12M 33/14 |
| | | | | 435/29 |
| 2016/0251247 A1 | 9/2016 | Chen et al. | | |
| 2017/0066696 A1 | 3/2017 | Appel et al. | | |
| 2018/0319713 A1* | 11/2018 | Wecker | ................... | C12P 21/00 |

FOREIGN PATENT DOCUMENTS

| | | |
|---|---|---|
| WO | 2007070452 A1 | 6/2007 |
| WO | 2010014797 A2 | 2/2010 |
| WO | 2013-171691 A1 | 11/2013 |
| WO | 2014097268 A1 | 6/2014 |

OTHER PUBLICATIONS

Prakash, "Non-Final Office Action", related to U.S. Appl. No. 14/932,218, dated Jul. 10, 2018.

Prakash, "Non-Final Office Action", related to U.S. Appl. No. 14/888,986, dated Jun. 13, 2018.

Beal, et al., "Energy Return on Investment for Algal Biofuel Production Coupled with Wastewater Treatment", Water Environment Research. 2012, vol. 84 No. 9, 692-710; abstract.

Gordon, "Response to Non-Final Office Action", related to U.S. Appl. No. 14/932,218, dated Dec. 28, 2017.

Liu, et al., "Pilot-scale data provide enhanced estimates of the life cycle energy and emissions profile of algae biofuels produced via hydrothermal liquefaction", Bioresource Techonology. 2013, vol. 148, 163-171; 165 Section 2 'Methods'; figure 2.

McCabe, "PCT Article 19 Amendment of Claims", related to International Application No. PCT/US2015/056344.

Prakash, "Final Rejection", related to U.S. Appl. No. 14/932,218, dated Nov. 31, 2018.

Prakash, "Non-Final Office Action", related to U.S. Appl. No. 14/932,218, dated Sep. 28, 2017.

Thomas, "International Search Report and Written Opinion of the International Searching Authority", related to International Application No. PCT/US2015-056344.

Young, "International Search Report and Written Opinion of the International Searching Authority", relating to PCT Application No. PCT/US18/67972, dated Mar. 25, 2019.

EPO, "Communication Pursuant to Rule 164(1) EPC", dated Jun. 4, 2018.

Schonwasser, "Provisional Opinion Accompanying Partial Search Result", dated Jun. 4, 2018.

Schonwasser, "Supplementary Partial European Search Report", dated Jun. 4, 2018.

* cited by examiner

Table 1. Energy return for biodiesel by feedstock and reference.

| Feedstock, reference | Energy return |
| --- | --- |
| Reclaimed vegetable oil | |
| Elsayed, et al. (2003) | 4.85-5.88 |
| Soybean oil | |
| Pimentel & Patzek (2005) | 0.78 |
| Carraretto, et al. (2004) | 2.090 |
| Ahmed, et al. (1994) | 2.5 |
| Sheehan, et al. (1998) | 3.215 |
| Hill, et al. (2006) | 3.67 |
| Pradhan, et al. (2009) | 4.56 |
| Sunflower oil | |
| Pimentel & Patzek (2005) | 0.76 |
| Edwards, et al. (2006) | 0.85-1.08 |
| Bona, et al. (1999) | 1.3-8.7 |
| ADEME & DIREM (2002) | 3.16 |
| Kallivroussis et al. (2002) | 4.5 |
| Rapeseed oil | |
| Edwards, et al. (2006) | 1.05-1.38 |
| IEA (1999) | 1.09-2.48 |
| Elsayed, et al. (2003) | 2.17-2.42 |
| ADEME & DIREM (2002) | 2.99 |
| Richards (2000) | 3.71 |

FIG. 9
(PRIOR ART)

SYSTEMS AND METHODS OF PRODUCING COMPOSITIONS FROM THE NUTRIENTS RECOVERED FROM WASTE STREAMS

RELATED APPLICATION DATA

This application is a continuation-in-part application of U.S. patent application Ser. No. 14/932,218, filed Nov. 4, 2015, and entitled "Symbiotic Algae System", which is a continuation-in-part of U.S. patent application Ser. No. 14/888,986, filed Nov. 4, 2015, and entitled "Symbiotic Algae System with Looped Reactor", which is a national stage application of PCT application no. PCT/US2015/056344, filed Oct. 20, 2015, which claims priority to U.S. provisional application Ser. No. 62/067,049, filed Oct. 22, 2014, and entitled "Symbiotic Algae System with Looped Reactor", U.S. provisional application Ser. No. 62/067,042, filed Oct. 22, 2014, and entitled "Symbiotic Algae System", and U.S. provisional application Ser. No. 62/079,135, filed Nov. 13, 2014, and entitled "Algal Growth System Process Utilizing Intermediate Products of Consolidated Bioprocessing Process or Anaerobic Digestion Process", each of which is hereby incorporated by reference herein in their entirety.

FIELD OF THE INVENTION

The present invention relates to algae growth systems and in particular to Systems and Methods of Producing Compositions from the Recovered Nutrients from Waste Streams.

BACKGROUND

Waste management, e.g., livestock manure, food wastes, beverage wastes, food byproducts, and nutrient runoff, are large environmental and societal concerns.

Livestock manure management is a global issue, with the U.S. Department of Agriculture estimating in 2012 that more than 335 million tons of "dry matter" waste (the portion of waste remaining after water is removed) was being produced annually on farms in the United States. Animal feeding operations annually produce about 100 times more manure than the amount of human sewage sludge processed and existing dairy manure management practices are unable to mitigate the environmental impact from nutrient runoff (a byproduct of anaerobic digesters). Food waste management is another large-scale global problem as about one-third of food is wasted worldwide. Food waste is estimated at between 30 to 40 percent of the food supply in the United States.

The successful role of algae in wastewater treatment has been documented since the early 1950s, and algal wastewater treatment systems are known to utilize the extra nutrients including nitrogen, phosphorus, potassium, heavy metals and other organic compounds from wastewater. For example, an algal turf scrubber system feeding algae a diet of dairy manure can recover over 95% of the nitrogen and phosphorous in the manure wastewater. Additionally, lipid/oil productivity occurs in algal wastewater treatment systems, but there are few, if any, known robust algae strain(s) for oil production that use wastewater as a primary feedstock. For example, a polyculture (dominated by *Rhizoclonium* sp.) used in algal turf systems for treating dairy and swine wastewater had very low lipids/oil content (fatty acids contents of 0.6% to 1.5% of dry algae weight) and other researchers have reported 2.8 g/m2 per day of lipid productivity from algal polyculture combined with dairy wastewater treatment.

Mass cultivation of algae has also been used for creating nutritional supplements, fertilizer, and food additives. Additionally, commercial growth of algae has been explored to create biologically-derived energy products such as biodiesel, bioethanol, and hydrogen gas. As a biofuel feedstock, algae provide multiple environmental benefits and presents significant advantages over traditional plants/crops used for biofuel production (e.g., corn, sugarcane, switch-grass, etc.). For example, unlike traditional food crops that are being used to produce biofuels (e.g., corn, sugarcane, etc.), algae does not compete with food and water resources; it grows significantly faster than traditional crops used for biodiesel; algae produce up to 300 times more oil than traditional crops on an area basis; algae fuel has properties (low temperature and high energy density) of which make it suitable as jet fuel; and algae can be produced so as to provide a nearly continuous supply of fuel. Moreover, algae can treat industrial, municipal and agricultural wastewaters, capture carbon-dioxide, and provide valuable byproducts, such as, but not limited to, protein-rich feed for farm animals, organic fertilizer, and feedstock for producing biogas.

Algal biomass can accumulate up to 50% carbon by dry weight, therefore producing 100 tons of algal biomass which fixes roughly 183 tons of CO2—providing a tremendous potential to capture CO2 emissions from power plant flue gases and other fixed sources for growing algae biomass. Ideally, biodiesel from algae can be carbon neutral, because all the power needed for producing and processing the algae could potentially come from algal biodiesel and from methane produced by anaerobic digestion of the biomass residue left behind after the oil has been extracted.

Algae's other byproducts can also be beneficial. For example, the value of algae as food was explored as early as 1950s, and some have demonstrated the concept by raising baby chickens to adults on twenty percent (20%) algae fortified feed (grown on pasteurized chicken manure). The antibiotic Chlorellin extracted from Chlorella during World War II marked the start of algae based pharmaceutical and nutraceutical industry that led to the Japanese *Chlorella* production facilities during 1960s, further leading to current production of *Chlorella, Spirulina, Dunaliella* and *Hematococus* at commercial scales. Fertilizers from algae have also shown equivalence to commercial organic fertilizers in terms of plant mass and nutrient content.

Despite all of the aforementioned benefits, algae biomass production and the production of algal oil (i.e., biofuels from algae) are primarily hampered by the high cost of producing algae biomass (currently either requiring large amounts of land/water and/or large sterile facilities). There have been attempts to offset this high cost by using the various traits of algae to their greatest benefit. For example, biofuel production from algae has been combined with waste-water treatment (as discussed above) and has been shown to be 40% more cost effective than the best conventional alternatives, but still has not been economically viable due to low lipid production. As another example, entities have attempted to vary the type of cultures used for example, algae monoculture (requiring sterile conditions) versus polyculture-based wastewater treatment. However, the results of these trials have not proven themselves, Other disadvantages of current algae biomass production include, but are not limited to, the availability of low cost throughput sugar feed-stocks for growing algae, treating effluent created during production, and the requirement of nitrogen and phosphorus supplements. Until such time as these algae production related issues are solved, production of oil feedstock from algae is likely to remain commercially infeasible.

For this reason, the system and process disclosed herein addresses the challenges involved in materializing the cost-efficient algae-based on a robust, easily adaptable, sustainable, environmentally friendly system that is capable of growing algae biomass at commercial scales for fertilizer, animal feed, water, biofuel, and other byproducts. The symbiotic algae system and process disclosed herein also holds great potential for farms, industries, and municipalities especially dairy farms and food & beverage industries, because the system allows these entities to more efficiently and effectively meet government standards for handling and recycling of wastes.

SUMMARY

In a first exemplary aspect, there is disclosed a symbiotic algae system comprising a pretreater suitable for producing a first effluent with reduced odor and biochemical oxygen demand; a first algal growth component fluidly coupled to the pretreater and receiving the first effluent, wherein the first algal growth component includes a heterotrophic algal growth strain, and wherein the first algal growth component produces a second effluent having nutrients and an off-gas; and a second algal growth component fluidly coupled to the first algal growth component, and the second algal growth component including at least one algal growth strain from the group of: a photoautotrophic algal growth strain, a mixotrophic algal growth strain, and a heterotrophic algal growth strain, and wherein the second algal growth component receives, as an input, the second effluent and the off-gas and produces a third effluent.

In another exemplary aspect, there is disclosed a symbiotic algae system comprising: a pretreater for producing a first effluent with reduced odor and biochemical oxygen demand; a first algal growth component, wherein the first algal growth component includes a heterotrophic algal growth strain, and wherein the first algal growth component produces a second effluent having nutrients and an off-gas; and a second algal growth component fluidly coupled to the first algal growth component, wherein the second algal growth component includes at least one algal growth strain from the group of: a photoautotrophic algal growth strain, a mixotrophic algal growth strain, and a heterotrophic algal growth strain, and wherein the second algal growth component receives, as an input, the second effluent and the first off-gas and produces a second effluent and a second off-gas; and wherein the second effluent and the second off-gas are received as inputs to the first algal growth component.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 9 is a table showing prior art energy returns for biodiesel using various feed-stocks;

DETAILED DESCRIPTION

Figure 1:
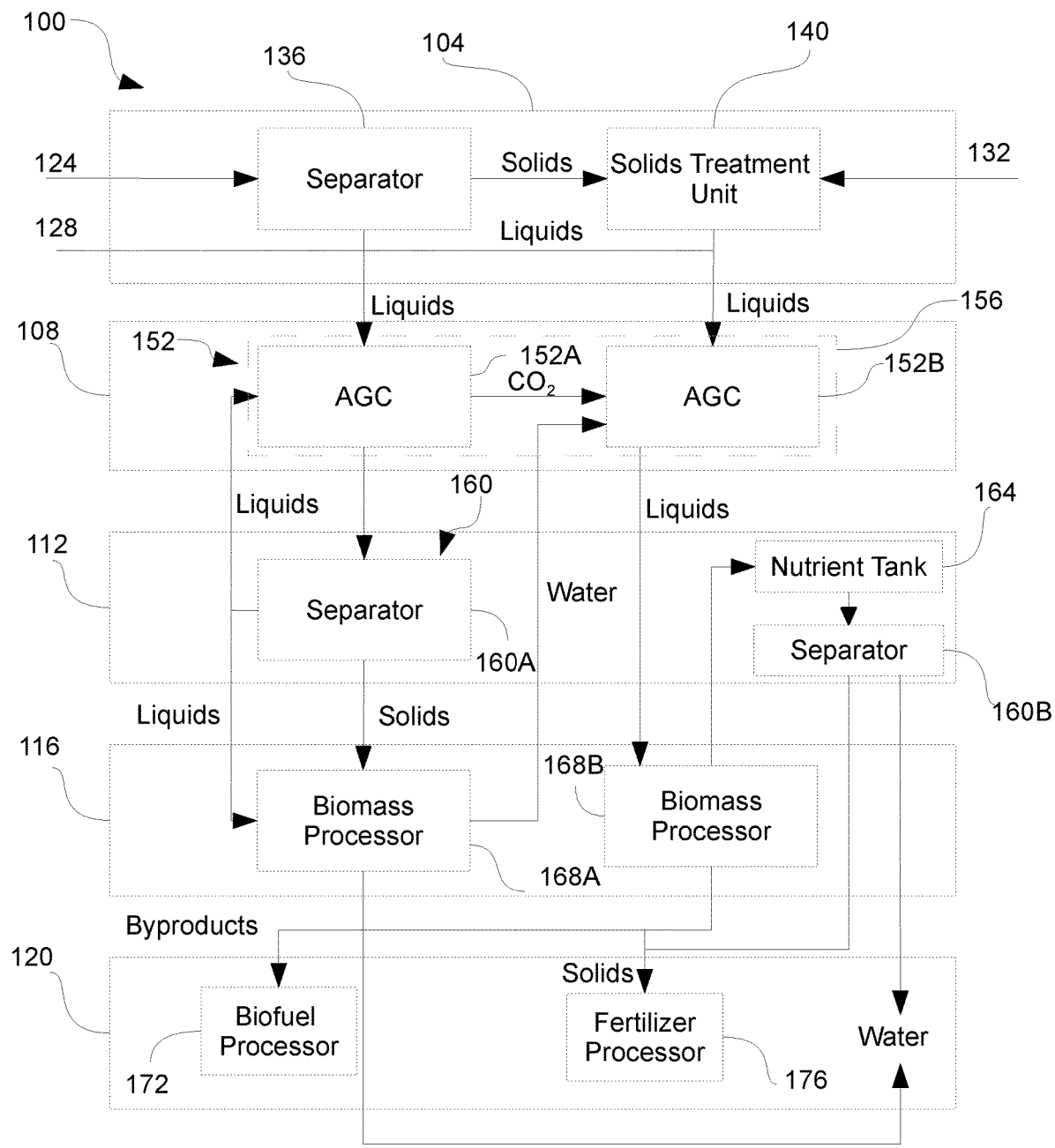
FIG. 1 is a block diagram of an exemplary symbiotic algae system according to an embodiment of the present invention.

Systems and methods disclosed herein can create useful compositions from the nutrients recovered from waste streams, such as, but not limited to, fertilizers for plant growth, soil fertility, and protein substitute for feed or food. The nutrients can be recovered by using one or more or combination of following: biological treatment in the form of biomass such as algae, as byproducts of mechanical and/or chemical separation of a waste stream, or chemical treatment.

Systems and methods disclosed herein use nutrients from various waste streams to produce compositions of valued byproducts such as fertilizer, animal feed, fuel, recycled water etc., where algae biomass production is one of the components. In certain embodiments compositions of fertilizer(s) or soil enhancement(s) for plant nutrition and soil fertility are created by using one or more waste stream processing byproducts. The byproducts can be produced through mechanical and/or chemical and/or biological and/or via anaerobic digestion or co-digestion processing of one or more waste components including, but not limited to: manure from livestock or animals, food waste from residential, or commercial or non-profit operations, beverage, byproduct(s) of beer or wine or alcohol or beverages or spirits, manufacture processes, source separated organic waste, organic byproducts of manufacturing processes, glycerol, glycerin, fats, oils, lipids, grease, yard waste, wood, biosolids, municipal material, digestible organic materials, and any combination thereof.

The byproducts of waste stream processing can include one or more or a combination of organic material including, but not limited to, separated and/or digested solids, fibers, non-fibers, effluent, exhaust gas(es), and heat. The byproducts can contain nutrient(s), either or combination of nitrogen, phosphorus, potassium and any or more of other elements such as Ca, Mg, Na, Al, Fe, Mn, B, Cu, Zn, S, Pb, Cd, As etc. The composition(s), created by the systems and methods disclosed herein, for plant nutrition and soil fertility include(s) predominantly aquatic biomass (such as algae, naturally occurring microorganisms, macrobial biomass like duckweed) grown with or without the byproducts of anaerobic digestion from the sources as described above. Systems and methods disclosed herein can also produce organic and/or non-organic byproduct(s) via mechanical and/or chemical and/or biological processing means such as, but not limited to, solids separation; centrifugation; dissolved air floatation; flocculation; struvite formation; enhanced biological phosphorus removal; crystallization of magnesium ammonium phosphate, calcium phosphate, incineration, bio-ammonium sulfate crystals and/or solids; combined nitrogen and phosphorus removal technologies; nitrification; denitrification; nitrogen and/or ammonia stripping with or without solid separation; separation of phosphorus and/or nitrogen and/or potassium rich solids; or biological conversion to non-reactive nitrogen and/or phosphorus. In some embodiments nitrogen and/or phosphorus may be present along with other non-predominant elements or compounds in various forms, structures etc. pH and/or nutrient balancing can be advanced by the addition of, for example, acidic or basic matter or a combination in nature such as lime, ash, tree parts, compost from any organic sources some described above.

In some of the embodiments described herein, systems and methods are disclosed for removing nutrients from agricultural and industrial waste streams so as to produce valued products such as fertilizer for plant growth and soil fertility, and protein substitute or supplement for animal feed. The systems and methods can, in certain embodiments, remove nutrient nitrogen and/or phosphorus in relatively high quantities—characteristics that limit other currently known technologies. Certain embodiments discussed herein can provide customizable compositions of valued products to serve needs of both front and/or end users and optionally, provide additional organic matter to support biological activity, build soil fertility, compensate for nutrient loss by crop harvest or runoff, slow release features to reduce nutrient runoff into waterways, and a wide variety of other applications.

A symbiotic algae system according to present disclosure provides a cost-efficient means of producing algae biomass for many applications, such as, but not limited to, as feedstock for biofuel manufacture and desirably impacts alternative/renewable energy production, nutrient recovery from waste streams, and valued byproducts production (nutraceuticals, pharmaceuticals, animal feed etc.). A symbiotic algae system as discussed herein is an integrated systems approach to wastewater treatment, algal strains selection for oil production, CO2 capture or nutrient capture from heterotrophic processes, and recycle of algal-oil extraction waste as feedstock for biogas production. Embodiments of a symbiotic algae system as discussed herein present an economically viable algae production system and process that allows algae-derived biofuels to compete with petroleum products in the marketplace.

A symbiotic algae system as discussed herein is, at a high level, a scalable process for cultivating algae biomass, in which a heterotrophic (i.e., non-light dependent) algal growth strain is used to provide carbon dioxide and/or effluent to a photoautotrophic or mixotrophic or a combination of the three cultivation processes (i.e., photoautotrophic, mixotrophic, and heterotrophic) while concomitantly producing algae biomass or lipids for biofuel production. In certain embodiments, the photoautotrophic or mixotrophic or heterotrophic cultivation portion of the symbiotic algae system may result in the cultivation of additional algae biomass, but could include (alternatively or additionally) the cultivation of any photoautotrophically or mixotrophically grown microbial plant matter that requires carbon dioxide and/or effluent containing nutrients, such as nitrogen, phosphorus and organic carbon. As will be discussed in more detail below, the symbiotic algae system can efficiently use nutrients from both commercial and/or other waste streams for the production of lipids for use with biofuels, and as such, the energy return on investment scenarios are significantly higher than previously considered possible. This symbiotic algae system provides a robust scalable option which has improved cost efficiencies due to production of additional desirable byproducts such as fertilizer.

Turning now to the figures, and specifically with reference to FIG. 1, there is shown a symbiotic algae system (SAS) 100. In an exemplary embodiment, SAS 100 includes, at a high level, a waste nutrient preparation sub-system 104, an algal culturing system 108, an algal harvesting system 112, an algal biomass processing system 116, and a byproducts system 120.

Waste nutrient preparation sub-system 104 is generally configured to treat incoming feedstocks (e.g., manure, municipal waste) for the rest of SAS TOO. The design and configuration of waste nutrient preparation sub-system 104 depends on the desired inputs for SAS 100. As shown in FIG. 1, waste nutrient sub-system 104 includes three inputs: an effluent input 124, a water input 128, and a waste input 132. Effluent input 124 can generally be any nutrient rich liquid waste before or after single or multiple pre-treatments, for example, dairy farm effluent, agricultural wastewater streams, brewery liquid waste streams, municipal waste, food waste, etc. Effluent input 124 is fed into a separator 136 that separates the effluent solids and liquids, using methods such as settling, filtration, or via centrifugal separators. The solids can then be fed to a solids treatment unit 140, such as a digester, which can, among other things, break down the solids into a feed stream suitable for further use within SAS 100, such as a source of carbon dioxide and sugars, or into other byproducts (e.g., biogas, fertilizers, etc.). Solids treatment unit 140 can also accept waste input 132 for processing solids treated by unit 140. The output of solids treatment unit 140 and the liquid effluent separated by separator 136 may be combined, with fresh water input 128 to prepare the feedstock for algae culturing system 108 that includes one or more algae growth components (AGC) 152, e.g., AGC 152A and AGC 152B.

In an exemplary embodiment, waste nutrient preparation sub-system 104 is a manure settling and solid's preparation unit that outputs liquid manure waste to algal culturing system 108. In this embodiment, manure is combined with water run-off (e.g., fresh water input 128) and collected in a large separation tank (e.g., separator 136). The denser solids are allowed to sink to the bottom (or in certain embodiments are mechanically separated) and the output liquid manure water is pumped from the tank. In an exemplary embodiment, solid wastes, for example, ligno-cellulosic material such as grain spoilage or grasses, is pretreated in solids treatment unit 140 with or without manure effluent to prepare the nutrients (e.g., different forms of nitrogen or phosphorus or sugars or organic carbon) for algal culturing in algae culturing system 108.

Figure 2:
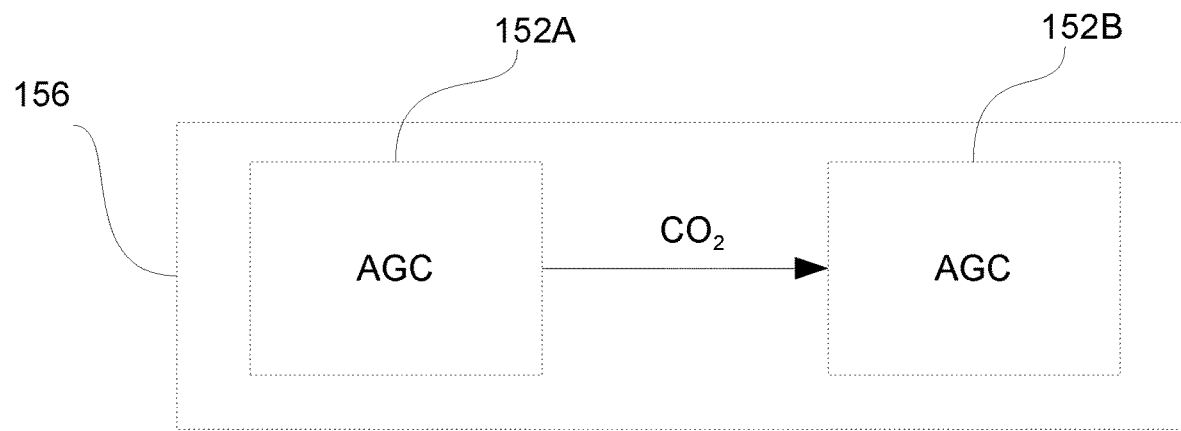
FIG. 2 is a block diagram of an algal core suitable for use with an exemplary symbiotic algae system such as the systems shown in FIGS. 1 and 5.

Algal culturing system 108 is generally configured to grow algal biomass from numerous nutrient and/or waste streams. In an exemplary embodiment, algal culturing system includes an algal core 156 (FIG. 2), which can include an AGC 152A that is coupled to, and mutually supports, an AGC 152B. In an exemplary embodiment, AGC 152A is an organic carbon source fed heterotrophic algae and AGC 152B is one or more of a photoautotrophic, mixotrophic, and heterotrophic algae. In general, heterotrophic algal production produces higher amounts of oil/lipids compared to its lighted dependent counterpart (e.g., mixotrophic, photoautotrophic), however it is limited in its ability to capture nutrients or other desired extracts and also generates effluent that typically requires treatment. Algal cultivating system 108 combines the two complementary approaches thereby providing a system that can produce high amounts of oil/lipids and can capture nutrients for byproducts such as fertilizer production that can offset the costs of algal biomass production. For example, the algae *Chlorella vulgaris* can remove up to about 20.8% of phosphate under autotrophic conditions, up to about 17.8% under heterotrophic conditions, and up to about 20.9% under mixotrophic conditions after 5 days when grown in synthetic wastewater. Algal culturing system 108, in certain embodiments described herein, can capture the remaining nutrients left after the heterotrophic algal growth stage and recycles these nutrients for the autotrophic/mixotrophic algal growth and vice versa. Additionally, algal culturing system 108 can also be designed to recycle the $CO_2$ produced as a result of heterotrophic mode of algal growth to the autotrophic/mixotrophic growth, and can recycle the oxygen produced by the autotrophic/mixotrophic growth for heterotrophic growth. The recycling of nutrients for different trophic growth provides additional cost offsets made possible via algal culturing system 108.

As discussed in more detail below, the design of algal core 156 determines the amount of algae produced in AGC 152B based on the amount of $CO_2$ produced by AGC 152A or vice versa with oxygen production by AGC 152A fed to AGC 152B. For example, if AGC 152A produces about 1.8 tons of $CO_2$, one would expect that up to about 1 ton of dry algae biomass would be produced by AGC 152B.

AGC 152A has the advantage of accepting a myriad of inputs. For example, and as described previously, AGC 152A can use liquid manure waste as in input, or can use organic carbon from commercially available clean sources (e.g. sugars) or other waste streams, such as but not limited to, grains spoilage from farms, brewery waste, liquids containing sugars from food waste, industrial wastes, or farm operation wastes, or a mixture of different wastes. Algal biomass production at AGC 152A can be maximized by using the naturally occurring or genetically enhanced algae strains, monoculture or polycuiture, and/or other microbial strains such as bacteria and/or fungi that is best suited for the feedstock (e.g. sugars available from market or from waste sources) available at the target location. In other words, certain algae do better with certain carbon inputs than others. In an exemplary embodiment, the algae, *Chlorella vulgaris*, has been successfully cultured in dairy manure effluents. In another embodiment, AGC 152A can use and produce non-algae strains, such as the fungal strain, *Trichoderma reesei*, for converting aforementioned throughput feedstock into byproducts.

In an exemplary embodiment, AGC 152A includes heterotrophic algae, which is known to produce dense algae growth and a relatively high amount of useful byproducts. Heterotrophic algae can be grown in fermenter(s), or closed or open system(s), or a combination or a hybrid form of the aforementioned. Standalone growth of heterotrophic algae is scalable in large sized vessels (such as, but not limited to, fermenters), and under heterotrophic growth conditions, respiration rates equal or exceed the theoretical minimum cost of biomass synthesis and biomass synthesis can achieve nearly the maximal theoretical efficiency.

One of the outputs (in addition to generated algal biomass for lipid extraction) of AGC 152A is an off-gas, $CO_2$, which is generated as a result of algae respiration due to organic uptake of carbon. The $CO_2$ generated by AGC 152A is used as an input for AGC 152B.

AGC 152B is designed to accept the output (which are typically byproducts) of AGC 152A. As such, AGC 152B can be a photoautotrophic, a mixotrophic, or a combination of both photoautotrophic and mixotrophic production systems of algae fed by the $CO_2$ produced by AGC 152A. AGC 152B can take the form of open, closed, or hybrid systems of algae growth and therefore can be implemented by various methodologies, such as, but not limited to, a tank, a bag, a fermenter, a tubular vessel, a plate, and a raceway, of any shape, size, or volume.

In an exemplary embodiment, AGC 152B uses clean sources of additional nutrients or captures nutrients from waste or wastewater streams, for example, but not limited to, anaerobically or aerobically digested effluent from dairy farms, industrial operations such as breweries, food waste, municipal waste, etc. The $CO_2$ input stream from various industrial operations, such as flue gases, supplied to second algal growth component 312 may contain other nutrients that promote algae biomass growth. While AGC 152B has been previously described as one or more of a photoautotrophic, mixotrophic, and heterotrophic algal growth, it could also include the cultivation of any biomass that requires the addition of inorganic carbon ($CO_2$) and/or organic carbon and/or nutrients (such as nitrogen and phosphorus and other micro or macro nutrients) for its growth.

In order to size algal core 156 (and ultimately determine an estimate of the total expected biomass (TEB) production of the system), the amount of algal biomass producible from AGC 152A at the site is determined based on the amount and type of throughput feedstock available, e.g., the amount available from on-site sources, brought from off-site sources, or combination of the two, to grow the respective algae type used in AGC 152A. For example, if the feedstock is nitrogen rich, algal types that may be paired with this feedstock include *Chlorella vulgaris, Chlamydomonas reinhardtti*, and *Secenedesmus abundans*. Alternatively, if the feedstock is phosphate rich, the algal types that may be paired with this feedstock include the bacteria *Acinetobacter calcoaceticus* or *Acinetobacter johnsonii*. Based upon the expected algal biomass producible from AGC 152A, an amount of $CO_2$ available to AGC 152B from AGC 152A can be determined. The available $CO_2$ and the amount of feedstock available to AGC 152B is determinative of the amount of biomass producible of AGC 152B. The TEB can then be determined as the sum of the algal biomass produced at AGC 152A and the biomass produced at AGC 152B.

The amount of biomass producible by either growth component, i.e., AGC 152A and AGC 152B, will be heavily influenced by the specific algae chosen for each respective component, and in the case of AGC 152B, the type of algae chosen. For example, a mixotrophic algal growth system requires less $CO_2$ because it requires greater organic carbon uptake when compared to a phototrophic system. Knowing the type of algal system chosen for AGC 152B (and the specific algae) can be used to determine the size or volume required for AGC 152B when implemented in the form of, for example, a closed photobioreactor, an open tank, a raceway, or a pond system. For example, for an output of 1000 tons of *Chlorella vulgaris* grown in AGC 152B (e.g. a photobioreactor) we would need at least 1800 tons of $CO_2$. That means we'll have to setup the AGC 152B system of the volume that can grow enough heterotrophic biomass that can produce 1800 tons of $CO_2$, because it is established fact that the photoautotrophic algae requires about 1.8 tons of $CO_2$ to produce 1 ton of algae. In case of mixotrophic algal production, the $CO_2$ requirement could be about 10 times lower.

In another embodiment the size of algal core 156 can be deduced inversely, e.g., first the maximum amount of biomass producible via AGC 152B on the site is determined (usually space/volume limited) based upon the type of algal system, inputs, and space/footprint available, then the $CO_2$ requirements of the AGC 152B are determined, which can then be used to determine the composition and size of AGC 152A.

In yet another exemplary embodiment of algal core 156, an oxygen rich air supply from AGC 152A (when implemented as a photobioreactor as a result of photosynthesis by photoautotrophic or mixotrophic algae) is fed into AGC 152B (when implemented as a heterotrophic reactor to support growth of heterotrophic algae). This arrangement solves a major well-known constraint in closed photobioreactor systems caused by excessive oxygen production which has an adverse effect on the algae growth inside the photobioreactor.

In a further embodiment, an AGC 152A feeds AGC 152B while AGC 152B feeds AGC 152, For example, AGC 152A may feed $CO_2$ to AGC 152B, while AGC 152B, concomitantly, feeds $O_2$ to AGC 152B. Additional $CO_2$ or $O_2$ can be fed to the respective components for additional biomass production and carbon capture as desired.

Of the many advantages offered by SAS 100 and specifically by algal core 156, is the scalable nature of the system. Scalability is enhanced because heterotrophic algae (i.e., AGC 152A) is capable of dense growth when compared to photoautotrophic algae and certain mixotrophic algae. While density allows for greater biomass production per volume, heterotrophic algal growth in AGC 152A produces an off-gas, $CO_2$, and effluent containing nitrogen, phosphorus, and other components requiring treatment before discharge. However, the need and concomitant expense of treatment can be mitigated (or even eliminated in certain embodiments) by incorporating AGC 152B because the second algal growth component uses the $CO_2$ and effluent created by the AGC 152A, thus significantly reducing waste treatment costs while producing additional algal biomass.

While algal core 156 has been described above as a part of a larger system, e.g., SAS 100, algal culturing system 108, etc., it can also be implemented as a standalone system.

Figure 3:
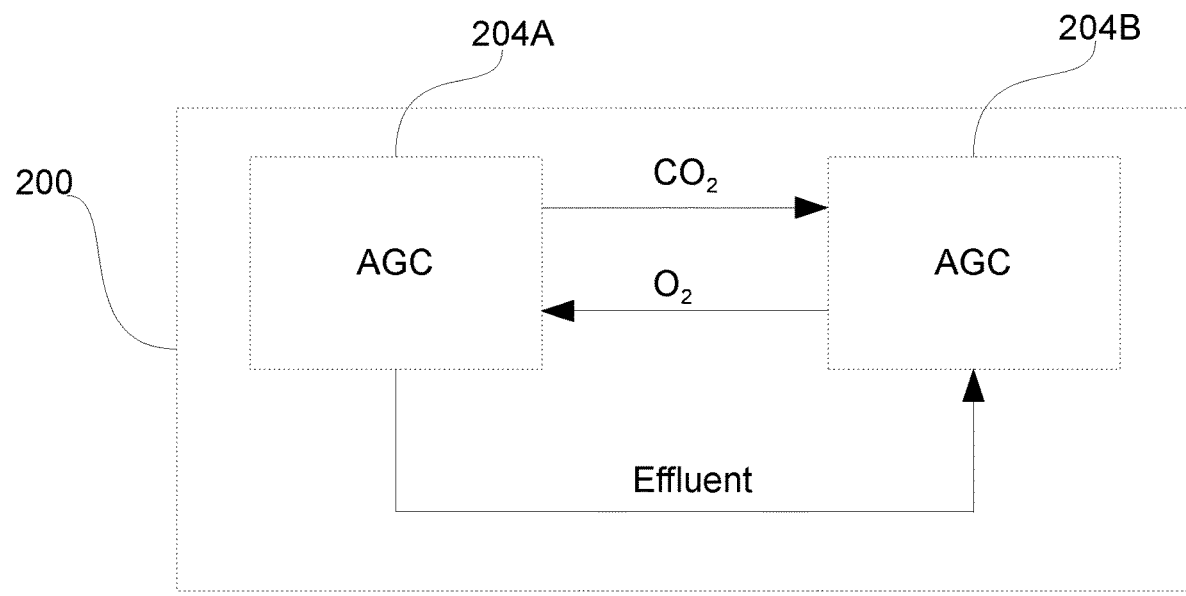
FIG. 3 is a block diagram of another algal core suitable for use with an exemplary symbiotic algae system such as the systems shown in FIGS. 1 and 5.

As shown in FIG. 3, an algal core 200 can also use post algal harvest liquid effluent obtained from AGC 204A as an input for AGC 204B so as to provide an additional supply of nutrients.

Figure 4:
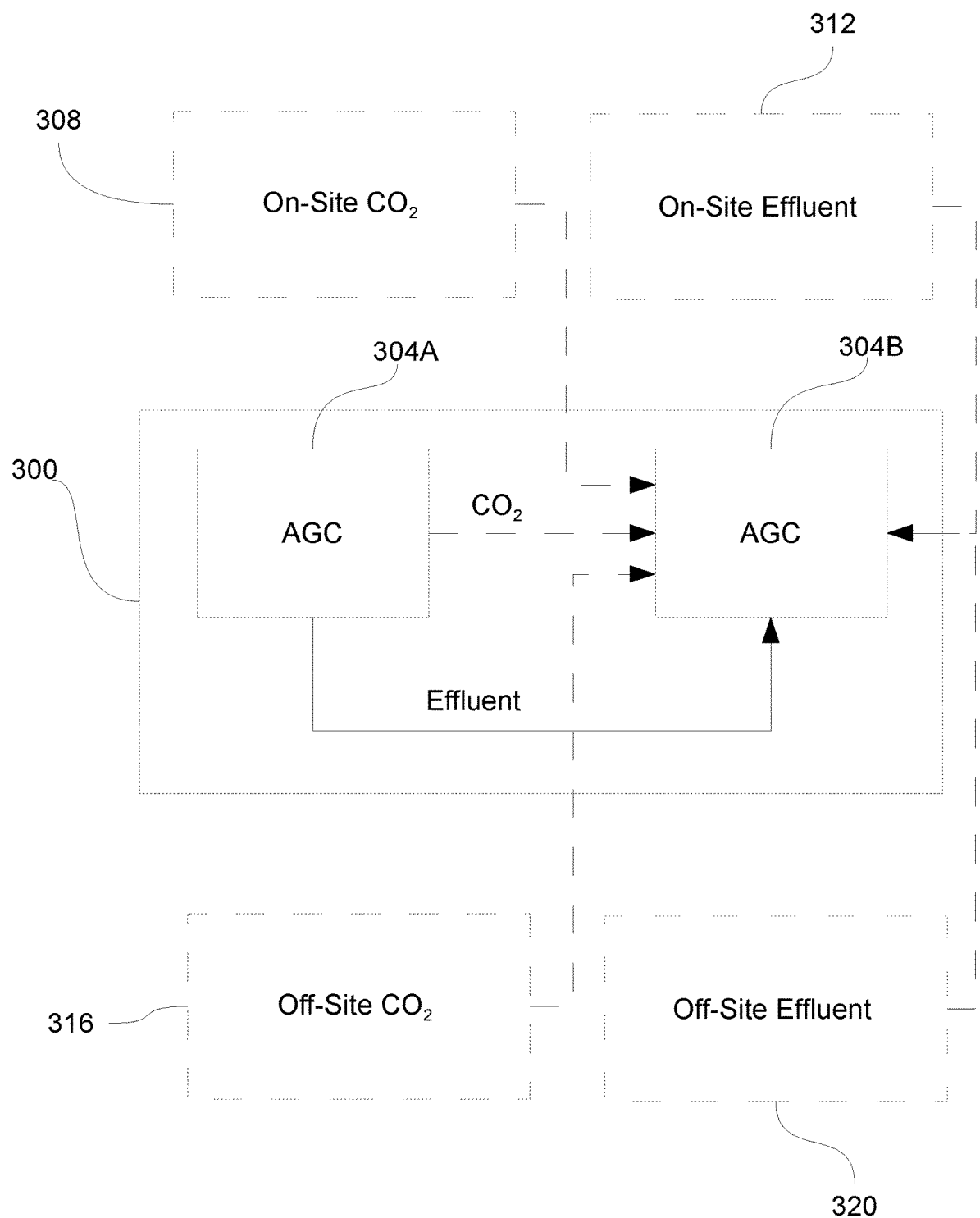
FIG. 4 is a block diagram of another algal core suitable for use with an exemplary symbiotic algae system such as the systems shown in FIGS. 1 and 5.
Figure 5:
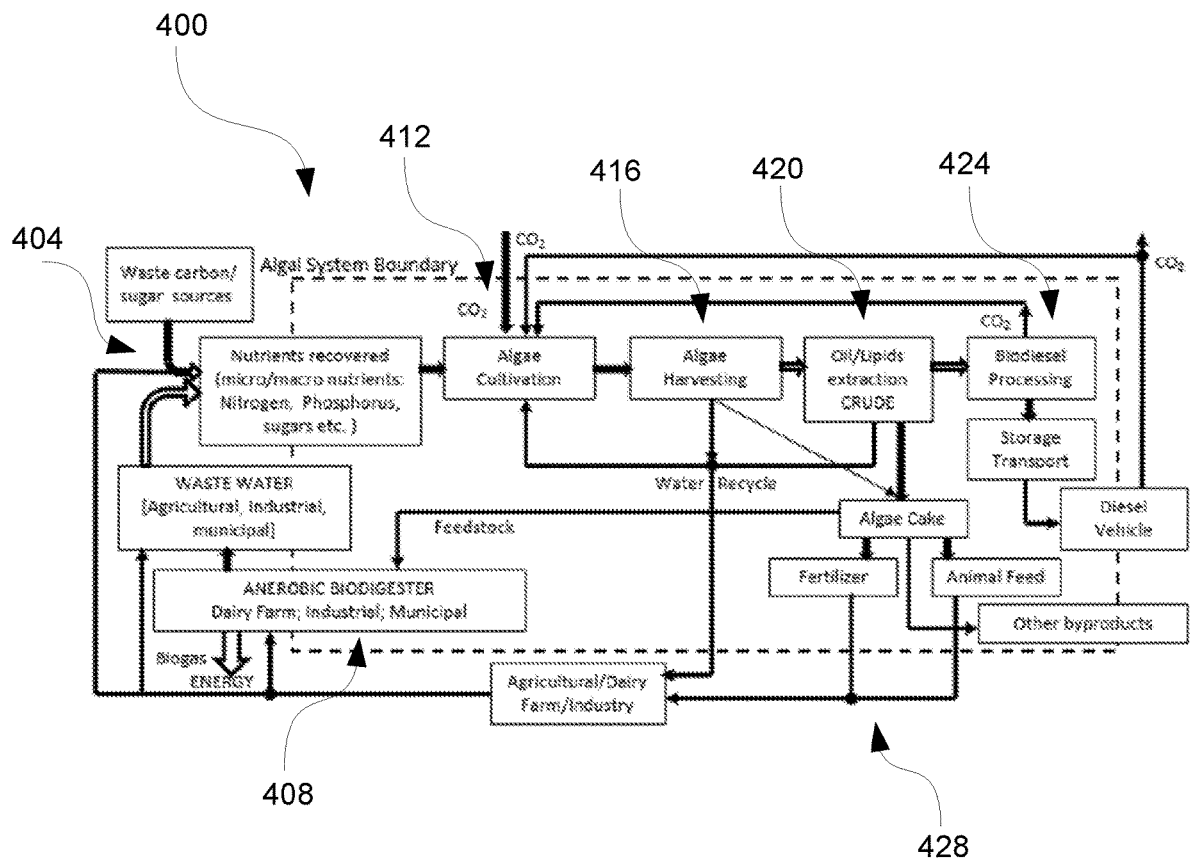
FIG. 5 is a block diagram of a portion of an exemplary symbiotic algae system according to another embodiment of the present invention.

In yet another embodiment of algal core 200, and as shown in FIG. 4, a first AGC provides nutrients, but little if any (optionally) $CO_2$ to a second AGC. This embodiment may be useful at sites where other means of $CO_2$ capture, e.g., fossil fuel emissions capture, are available. Advantageously, using an algal core of this embodiment may also assist a $CO_2$ emitting facility keep $CO_2$ emissions within emission limits as the excess $CO_2$ can be fed to one of the AGC's.

Another embodiment of algal core, algal core 300, is shown in FIG. 4. In this embodiment, algal core 300 includes a pair of AGC's, AGC 304A and 304B. AGC 304B is optionally fed with various sources of $CO_2$ from either onsite resource 308, off-site resource 312, or from AGC 304A, or combinations of two or more of these $CO_2$ sources. For example, at a dairy farm, the anaerobically digested effluent containing nitrogen and phosphorus is on-site resource. The supplementary nutrient source from off-site could be the effluent from a creamery, cheese factory etc. FIG. 4 also shows AGC 304B being fed with additional sources of nutrients from either onsite resource 316 or off-site resource 320, including, but not limited to industrial waste, brewery waste and/or surplus, food waste and/or surplus, farm waste and/or surplus, and/or municipal waste.

Returning now to a discussion of FIG. 1, algal harvesting system 112 is used to collect the algal biomass generated by algal culturing system 108. In an exemplary embodiment of algal harvesting system 112 includes one or more solid separators 160, e.g., solid separator 160A and 160B, and a nutrient tank 164. Whether or not the output of AGC 152A or 152B should be sent to a separator 160 is determined by the type of output produced by the AGC. In an exemplary embodiment, and as shown in FIG. 1, AGC 152A produces a relatively low concentration algal biomass and thus separator 160A is used to concentrate the output of the AGC. In contrast, in an exemplary embodiment, AGC 152B produces a relatively concentrated algal biomass output that can be sent directly to a biomass processor 168 (described in more detail below)

When algal harvesting system 112 is in use, algae biomass from AGC 152A is provided to solid separator 160A, which in this embodiment is a settling tank that allows the algae mass to settle to the bottom of the tank. In this embodiment, the bottom quarter of the settling tank (or so) is then physically separated from the rest of the settling tank's contents. The top ¾ of the settling tank (generally a liquid layer) is pumped out of solid separator 160A (and can be re-fed into either AGC 152A or AGC 152B, or sent to algal biomass processing system 116, as discussed below) leaving only the bottom algae concentrate which can be subsequently removed.

Algal solids (also referred to as concentrate) separated out by algae harvesting system 112 are sent to algal biomass processing system 116, which can be a standalone unit or a combination of Centrifugation, Filtration, Drying, Gravity settling, Microbial or Chemical based biomass aggregation, Flocculation and Sedimentation etc., to concentrate the algal solids. As shown in FIG. 1, algal biomass processing system 116 includes a pair of biomass processors 168 (biomass processors 168A and 168B). In an exemplary embodiment, biomass process is implemented as a separation funnel tank equipped with electrodes. In this embodiment, the algae concentrate from algal harvesting system 112 is gravity fed into the separation funnel tank. A current is then run through the algal concentrate, via the electrodes, causing individual algae cells to burst thereby releasing the lipids inside. The mixture within the separation funnel tank can then be allowed to separate into three layers, a solid layer (also referred to as "cake" layer), a water layer, and a lipid layer. The separation funnel tank can then be used to individually remove each layer for further processing or use. In another exemplary embodiment, biomass processing system 116 harvests algae from man-made water collection structure such as tanks, pits, ponds etc., or natural water bodies such as ponds, tributaries, lakes etc. in addition to being a part of SAS 100. The harvested algae can be become part of the algae cake and/or processed for different byproducts production such as fertilizer. In exemplary embodiments, biomass processing unit 116 is implemented as a centrifuge, or as a unit that is immersed or floats on water to harvest biomass. For instance, a biomass processing system 116 can be installed at a farm that has nutrient runoff collection pits installed, which captures farm runoff and thereby naturally produce additional algae and microbes. A biomass processing unit 116 can harvest these algae and microbes and add them to the algae cake. Algae cake with or without the addition of wild or naturally occurring algae can be dried or mixed with additional biomass for conversion into biofuel. In some of the instances of biomass processing unit 116 the algae cake is densified by the addition of a secondary material or a mix of materials such as sawdust, hay, grasses, pelletization or pucks waste or surplus, lumber waste or surplus, wood waste, or surplus etc. These densification processes may be beneficial to the renewable diesel production processes described below, to the formation of a storable form of fertilizer, or for the creation of combustible algal pellets for burning in gasifiers for heat. In some instances, algae cake alone or mixed with one or several materials, as described above, is pelletized or prepared into pucks, briquettes, pellets, etc., thereby providing increased storability. In another embodiment, algae cake is mixed with grasses grown on wasteland, or in buffer zones for capturing nutrients, e.g., miscanthus, switchgrass, etc., and then is formed into pellets, briquettes, pucks, etc.

Byproducts system 120 further treats the outputs received from algal biomass processing system 116. In an exemplary embodiment, from the lipid layer, crude algae oil is extracted with a solvent and a catalyst through a suitable process (chemical or non-chemical) at biofuel processor 172 so as to produce biodiesel and glycerol. In another exemplary embodiment, algae cake is converted into different forms of marketable fertilizer (either or both liquid and solid types). The solid fertilizer can be made into different forms such as powder, granular, pelleted, etc. and can include different proportions of nitrogen, phosphorous, and potassium (commonly combined and referred to as N—P—K). Producing algae fertilizer with marketable N—P—K concentrations has proved elusive. However, in certain embodiments of SAS 100, different algae types (monocultures, polycultures or aggregations of naturally occurring algae with or without other microbes or components), capable of capturing different fertilizer constituents (e.g., N, P, K), are grown separately either in the looped reactor or in combined or stand-alone autotrophic, mixotrophic or heterotrophic reactors or open ponds. Harvested algae can then be mixed in different proportions to obtain the marketable equivalent compositions of N—P—K, for example as in, Alfalfa meal (N—P—K: 2-1-2); Soymeal (7-2-1); and chicken manure (1.1-0.8-0.5). Algae fertilizer can also be enhanced by blends of different commercially or locally available materials for example, by adding trace minerals for creating algae-based seed starting mixes, or by adding potassium for creating certain desirable N—P—K composition. Granular fertilizer can be made using fertilizer processor 176, which, in an exemplary embodiment is a commercially available granulating machine. In an exemplary embodiment, algal cake with sufficient moisture is dried prior to granulation. It has been reported that solid form of fertilizer applications improve crop growth by providing the captured nutrients in a relatively stable and storable form, which is not possible with application of liquid manure on the land via manure spreader. This inefficiency exists, because there are only few time windows available for liquid manure spreading during the crop growth. However, using a storable, granulated form of algal-based fertilizer provides flexibility of application during the times when manure spreader cannot be used, such as for dressing the corn plants at the appropriate stage of their development. An environmental benefit, among others, of removal of nutrients via algal fertilizer is the reduction of nutrients runoff into natural water bodies. Moreover, cost offsets would be economically beneficial as fertilizer production produces an income stream for the farms or other businesses.

In yet another embodiment of byproducts system 120, biofuel processor 172 can convert algal biomass directly from algal culturing system 108, or through algal harvesting system 112, or algal biomass processing system 116 into 'renewable diesel' and byproducts via hydrogenation (treatment with addition of hydrogen) via processes such as, but not limited to, a) hydrothermal processing (for instance, by reacting the biomass on the order of 15 to 30 minutes in water at a very high temperature, typically 570" to 660° F. and pressure 100 to 170 atm standard atmosphere, enough to keep the water in a liquid state to form oils and residual solids); b) indirect liquefaction (for instance, a two-step process to produce ultra-low sulfur diesel by first converting the biomass to a syngas, a gaseous mixture rich in hydrogen and carbon monoxide, followed by catalytically conversion to liquids, the production of liquids is accomplished using Fischer-Tropsch (FT) synthesis as applied to coal, natural gas, and heavy oils); c) integrated catalytic thermochemical process such as integrated hydropyrolysis and hydroconversion (IH2); d) hydroprocessing (the hydrothermal liquefaction (HU) of biomass provides a direct pathway for liquid biocrude production via two types of methods possible for conversion of fatty acids to renewable diesel: "high-pressure liquefaction" or "atmospheric pressure fast pyrolysis").

Potable fresh water is produced as a byproduct of algal harvesting system 116 that can be recycled for other uses.

EXAMPLE

In this example, an algal core included a first algal growth component that was a heterotrophic component that included a heterotrophic algal strain and which generated and ted carbon dioxide to a second algal growth component was a photoautotrophic counterpart that included a photoautotrophic algal strain. It should be noted that the latter could be a, photoautotrophic open pond/tank, or a hybrid system supporting photoautotrophic or mixotrophic growth.

Two sets of bioreactors were setup to represent a test (an embodiment of the algal core discussed above) and a control. The control system was a closed photobioreactor fed with ambient air. The test algal core included two closed reactors, a heterotrophic reactor and a photoautotrophic reactor (supporting heterotrophic and photoautotrophic algal growth, respectively), where the photobioreactor was connected to ambient air supply plus the additional carbon dioxide generated from the heterotrophic reactor produced as a result of fermentation process. Both control and test systems were run in duplicate under the same temperature conditions, utilized artificially prepared media, and algae inoculums (also referred to as algae starter). In this experiment, when compared to the photoautotrophic counterpart, only half of the amount of algae starter was used in the heterotrophic reactor so as to maintain control over the heterotrophic reactor process.

For the heterotrophic reactor, additional glucose was added to the artificial media, and the reactor was run without exposure to light. The photobioreactors had the same constant light supply in both the test and the control batches. All reactors were regularly monitored for optical density, which indicates algal density (process discussed and shown in FIG. 6). Algal lipid content was monitored at the end of the log phase (day 4) and thereafter via confocal scanning laser microscope—a state-of-the-art multi-spectral imaging system using lipophilic dye. It was observed that the lipid content in the algal cells was negligible on day 4 and was highest on day 7 making it reasonable to harvest biomass on day 7. It should be noted that algae density can be strain and inoculum specific as some algae cultures may surpass the log phase earlier than 4 days, thereby making the harvest possible earlier than as shown in this example.

Figure 6:
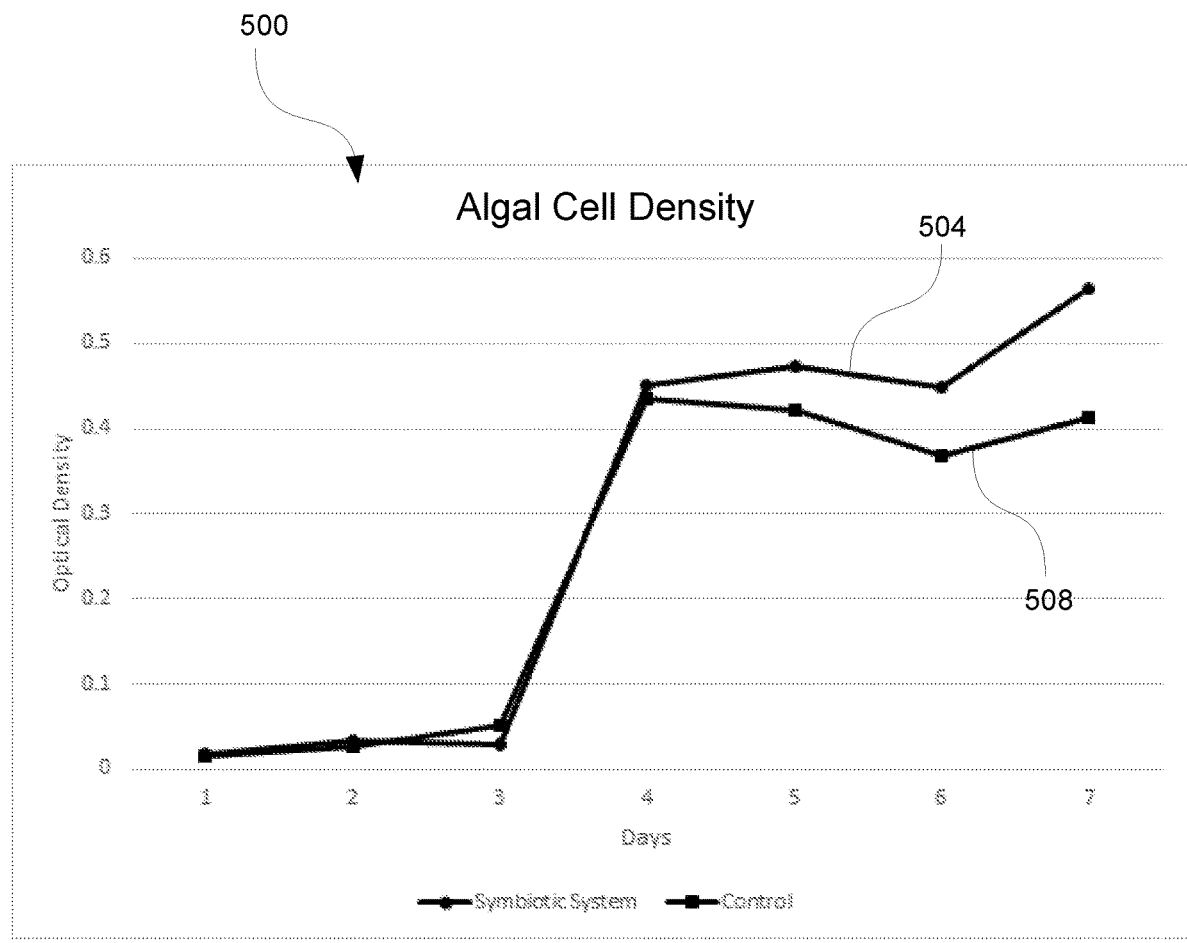
FIG. 6 is a chart of algal cell density showing the optical density over time for a test core according to an embodiment of the present invention and a control.

FIG. 6 shows a chart 500 of algae density (as measured by optical density) over time in days. Line 504 represents the test reactors and line 508 represents the control. As shown, very little algal density exists prior to day 4. After day 4, however, optical density substantially increases for both systems; however, algal density of the test system outpaces the control.

On the harvest day (day 7), the algal growth in the test algal core was found to be about 1.37 times higher (i.e., 37% more) than in the control reactor, which is considerable when extrapolated. For example, a typical harvested photoautotrophic algae on dry weight basis is in the range of 300 mg/L (0.3 gm/L) to 1 gm or more in photobioreactors. Using the more conservative harvest estimate, i.e., the 0.3 gm/L scenario, and extrapolating to an exemplary and typical 2000 ton/day algal growth system, a conventional photobioreactor system (or open pond system) would produce about 728,000 tons of algae biomass for oil extraction annually, whereas the photoautotrophic algal biomass harvest in the algal core, as discussed above, would be about 994,728 tons-a 266,728 ton surplus harvest.

As noted above, the heterotrophic reactor received 50% of the algae starter compared to the photobioreactor; however, if both reactors included an equal amount of algal inoculum the amount of surplus algae from the heterotrophic reactor would be expected to double due to additional carbon dioxide generated by the heterotrophic reactor. If double the amount of heterotrophic algae was grown in the symbiotic system this would contribute a surplus harvest of 3-4 times greater from the photobioreactor, thereby making the final surplus outcome about two or three times the harvest (i.e., about 74% to 111% more than the control). This example also illustrates how the volumes of the heterotrophic and photoautotrophic components in the symbiotic system could be customized to the algal harvest required from the two respective components. The surplus algal biomass generated could vary (lower or higher) in some embodiments depending on other factors such as media composition, light exposure, algae strain etc.

The examples and embodiments presented above could be applied to a variety of seed trains, where one system feeds a scaled up version of the system. Various combinations of an SAS, such as SAS 100, could be made with the other existing algal growth systems and/or microbial growth systems.

Looped Algae Reactor Design Pattern (LARDP)

Figure 7:
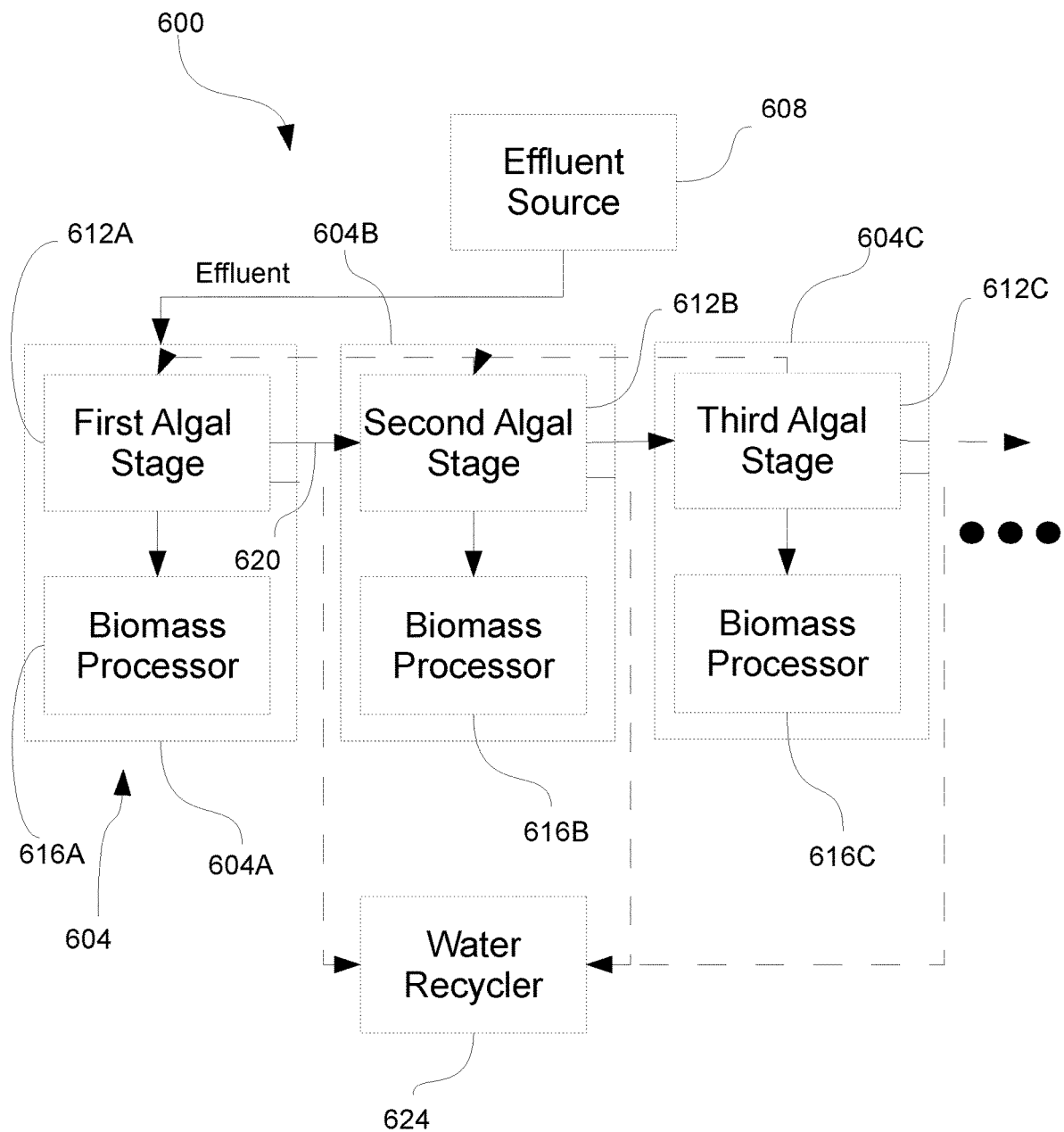
FIG. 7 is a block diagram of a portion of an exemplary symbiotic algae system suitable for removing contaminants according to another embodiment of the present invention

SAS 100 can, in certain embodiments, include a Looped Algae Reactor Design Pattern (LARDP) 600, as shown in FIG. 7. LARDP 600 is a process and/or a system that can be added/attached to algal cultivating system 108, algal cores 156, 200, or 300, or can be a standalone system attached to a waste treatment, wastewater treatment, remediation system for cleaning wastewater/effluent streams using one or more strains of microalgae (or other microbial organisms such as bacteria, fungi etc.), or to any algae-based or microbial-based process producing a target product or byproducts. At a high level, LARDP 600 uses a process of repeated cultivation of algae for co-product development and/or removal of nutrients for improving water quality of the effluent stream by growing algae biomass with or without other microorganisms.

LARDP 600 can include a series of nutrient extraction systems (NES) 604, such as first NES 604A and second NES 604B. Each NES 604 is designed to extract a certain type or types of components from an incoming effluent source 608, such as an algal effluent stream from an algal growth component, such as AGC 152A or 152B, or from other sources described herein. In an exemplary embodiment, first NES 604A includes a first algal stage 612 that receives, as an effluent stream as an input. First algal stage 612 is sized and configured to use microorganisms, such as those previously described herein, to extract from effluent stream 608 a certain type or types of components, such as, but not limited to, a nitrogen, a phosphorus, a heavy metal, a toxic component, a particular element (e.g. Ca, K, Mg, Na, Al, Fe, Mn, B, Cu, Zn, S, Pb, Cd, As), a complex element such as an antioxidant (e.g. astaxanthin), and a nuclear component. First, algal stage 612 allows for the growth of the microorganisms and, in certain embodiments, can be similar in design to AGC 152B. At a desired time, the algal biomass produced by first algal stage 612 is harvested at biomass processor 616, which can be performed as described above. First algal stage 612 also produces an effluent 620, which is at least partially devoid of the component that first algal stage 612 was designed to remove. This effluent can proceed to one or more primary pathways. The effluent can 1) be recirculated back to first algal stage 612A for further extraction of components (not shown), 2) proceed to a water recycling unit 624 for further water treatment, 3) proceed to second algal stage 604B, and/or 4) return to algal cultivating system 108 (FIG. 1) (when LARDP 600 is coupled to such a system). In general, the concentration of the dominating component in the effluent 620 determines its destination, example, if first algal stage 612 contained predominantly the alga *Chlorella vulgaris* which removed certain amount of nitrogen and phosphorus such that effluent 620 contains almost no nitrogen but still contained phosphorus, the effluent would likely travel to the 612 system containing the microorganisms capable of utilizing phosphorus more efficiently than *Chorallla vulgaris*, such as, but not limited to *Oscillatoria* sp.

Second NES 604B and third NES 604C can be sized and configured to remove the same or a different type of component than that removed form first NES 604A. Second NES 604B thus can similarly include, a second algal stage 612B and a biomass processor 616B, and similarly third NES 604C can include, a third algal stage 612C and a biomass processor 616C. Additional stages 604 can be included to further extract components from effluent streams and recirculation to each stage in place in LARDP 600 can be performed. For example, if at first NES 604A, a first heavy metal is removed such that after entering the first NES it is present in the effluent stream in a lower concentration, the effluent can proceed to second NES 604B where another component, for example, a second heavy metal is removed to a lower concentration. The effluent from second NES 604B can then be recirculated to the first NES 604A for further removal of the first heavy metal, which is facilitated by the lower concentration of the second heavy metal.

In another exemplary embodiment, LARDP 600 is sized and configured to produce organic fertilizer from effluent steam 608. In this embodiment, at each NES 604 a desired fertilizer component is removed, e.g., nitrogen, phosphorous, potassium, etc. As each NES 604 allows for the harvesting of a concentrated amount of the desired component that is entrained within the organism, e.g., algae, in the NES, specific and fairly pure amounts of the component can be harvested and then mixed together to obtain the desired fertilizer product.

In use, when attached to an algal system, such as algal culturing system 108, microalgae disposed within LARDP 600 is cultivated in the effluent generated by the algae growth system. In this embodiment, LARDP 600 is designed to remove undesirable substances such as, but not limited to, unwanted nutrients (e.g., nitrogen and phosphorus) and heavy metals. The biomass resulting from LARDP 600 can then be harvested from the wastewater and, depending on what LARDP has been designed to extract, processed to produce useful products such as, but not limited to, fertilizer and compost, or can be used as feedstock for digesters producing energy such as biogas or bio-electricity. After removal of the undesirable substances as described above, the remaining wastewater can then be further treated by cultivating the same or a similar strain of microalgae as used in algal growth system 108 for producing the primary product, or the remaining wastewater can be further treated by one or more different algae strain(s) used as a monoculture or a polyculture with or without other microorganisms such as bacteria or fungi to further remove nutrients (e.g., nitrogen and phosphorus) or heavy metals or any other undesirable components present in the wastewater generated. LARDP 600 can be repeated in one or more stages with same or different strains of algae and/or bacteria and/or fungi or any other organisms compatible with algal strains, grown as a monoculture or polyculture in any type of algal growth system until the desired level of water quality is reached.

The number of NES 604s used in LARDP is determined by the number of desired removable elements in the effluent(s) that require capturing using microalgae or microbes and the desired water quality.

In an embodiment of the system, the one or more 604 stages in LARDP can be optionally combined or replaced by other processes such as multiple screening systems, decanting centrifugation, polymer flocculation, ammonia stripping, struvite formation, nitrification/de-nitrification, etc. Modifications of these processes can also be used for enhancing the whole process of nutrient removal.

LARDP 600 can be useful in the creation of products, including, but not limited to, biofuels, fertilizer, animal teed, and cosmetics. The organisms cultivated in LARDP 600 can be cultivated under a green house or other similarly enclosed environment, so as to prevent contamination by competitive microorganisms while admitting light. LARDP 600 can be implemented in, for example, vertical freestanding tanks, raceway style ponds, or tracks.

Additional useful byproducts from SAS 100 include the production of clean carbon dioxide (as compared to the CO2 captured from flue gases) generated from an algal growth component, such as AGC 152A, which, while discussed previously as supporting AGC 152B, can also be captured and used for other applications needed a clean source of CO2, e.g., medical applications, electronics, laboratories, etc. Alternatively, the CO2 can be used for algal inoculum-preparation (a highly concentrated algae culture typically used for seeding a larger scale system) especially to generate light-dependent inoculum for seeding a system or sub-system.

Figure 8:
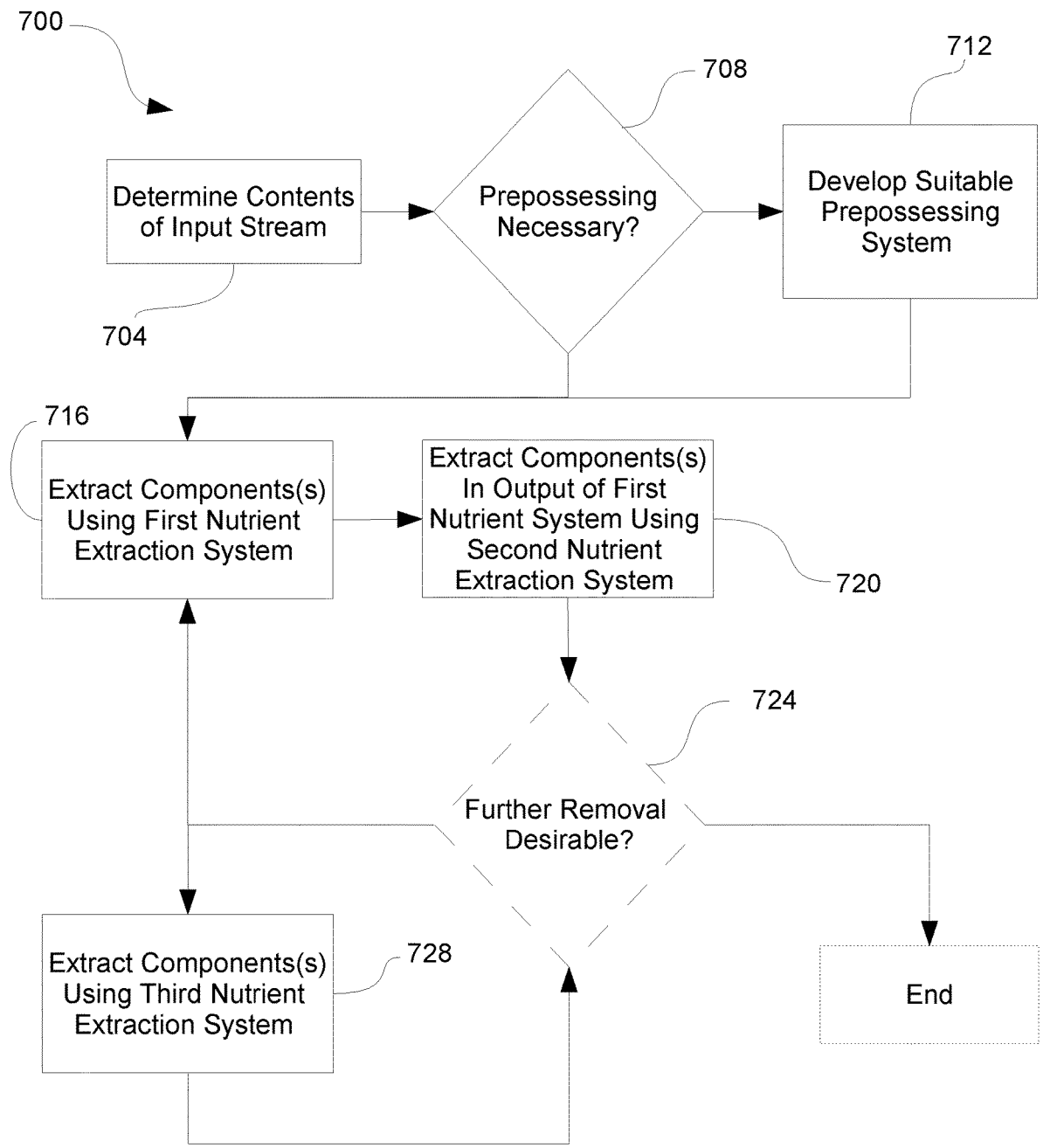
FIG. 8 is a block diagram of an exemplary process of removing contaminants from a waste stream according to an embodiment of the present invention.

FIG. 8 shows a process 700 for removing contaminants from a waste or effluent stream. At step 704, the content of the waste or effluent stream is determined. While typical nutrients, such as nitrogen and phosphorous are likely to be found, the stream may also include heavy metals or other nutrients that are desirably removed from the stream before the stream is put to further use or otherwise treated. Determining which nutrients and other particles are a part of the waste or effluent stream will assist in determining the type of nutrient extraction system, such as one of the NES 504s discussed above, to implement.

At step 708 it is determined whether any preprocessing is necessary prior to the stream entering the first NES. Preprocessing may be necessary if the stream contains significant solids or too much liquid. If preprocessing is necessary, process 700 proceeds to step 712 where a suitable preprocessing system is developed. Exemplary preprocessing systems are solids treatment unit 140 and separator 136 as discussed above with reference to FIG. 1. If no preprocessing is necessary, process 700 proceeds to step 716.

At step 716, a first NES is used to extract components from the waste or effluent stream. In an exemplary embodiment, first NES is sized and configured to focus on a relatively small number of components for extraction. For example, if the input waste or effluent stream is nitrogen rich, first NES may be configured to include an algal component that is primarily effective at removing a substantial portion of the nitrogen from the waste or effluent stream. The output of first NES is then provided to a second NES at step 720 for extraction of another component of the original waste or effluent stream.

At optional step 724, a determination is made as to whether further removal of nutrients from the output of step 720 is desired. As part of step 724, a determination of the composition of the output of step 720 may be completed and may be used when the effectiveness of steps 716 and 720 and may be necessary so as to determine where, if anywhere, the output of step 720 should be sent. For example, in order to effectively remove a heavy metal from a waste stream, it is generally beneficial to remove nutrients that are in the stream in significant amounts. Therefore, if, for example, the output of step 720 included significant amounts of a nutrient, e.g., nitrogen, which would render extraction of the heavy metal difficult or inefficient, step 724 would determine that the stream should be sent to an NES that will efficiently remove more nitrogen (e.g., step 716). However, if removal of a different component is desired, process 700 may proceed to step 728 where a third NES is used to extract components form the output stream. If no further extractions are necessary, the process ends.

Turning now to a discussion of FIG. 9, there is shown energy return values (EROI) for biodiesel by feedstock. The EROI is calculated as the ratio between the energy produced and the energy consumed by a system, and is generally considered a critical measure for evaluating the net energetic profitability of that system. As the EROI increases, the energetic profitability of that energy system also increases. For any feedstock (e.g., algae, soybean oil, etc.) or combination of feedstocks (e.g., SAS 100) to be a net energy source, the EROI to operate the entire associated production system(s) must be greater than 1. However, historically, the EROI of viable energy sources has been much greater than 1 and, therefore, practical deployment of an energy source typically requires an EROI much greater than 1. For instance, the EROI has been used to characterize several conventional fuels; for example, for coal, oil and gas, and corn ethanol, the second-order EROI has been estimated to be ~80 (at the mine), ~15 (at the well), and ~1 (at the biorefinery). Delivered gasoline (considering the entire supply chain) has reported an overall EROI of around 5 to 10.

As shown in FIG. 9, the EROI range is a low of 0.76 for sunflower oil to a high of about 5.88 for reclaimed vegetable oil. In comparison, certain embodiments of SAS 100 (varying pretreatment and algae types) obtained an energy return values of about 1, 11, and 40. Under certain conditions it can go even higher.

Figure 10:
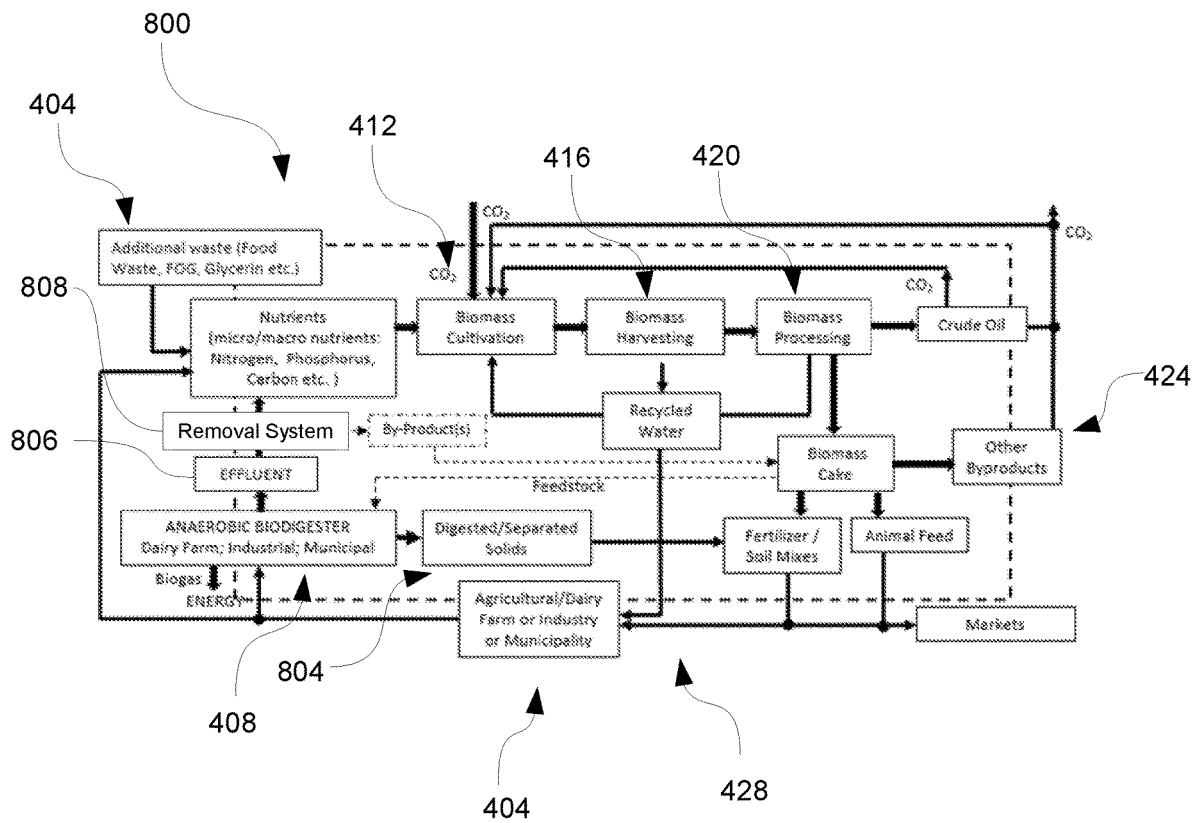
FIG. 10 is a block diagram of an exemplary symbiotic algae system according to another embodiment of the present invention.

Turning now to FIG. 10, there is shown another exemplary symbiotic algae system, SAS 800, according to an embodiment of the present disclosure. At a high level, SAS 800 is similar in many respects to SAS 400, and as such, unchanged/substantially similar components have been numbered according to SAS 400. SAS 800 includes, but is not limited to, acquiring of feedstock inputs 404 from, for example, stakeholders, pretreater 408, solids separator 804, algae cultivator 412, biomass harvester 416, oil extractor 420, byproducts manufacturer 424, and recycling of materials 428. Feedstock inputs 404 may be from a variety of stakeholders external to the SAS 400 operators, such as dairy manure waste generated at a farm (or in case of an industrial process, such as brewery, its generated wastes). Feedstock inputs 404 are processed through pretreater 408, which can be an anaerobic digester that in addition to generating effluent useful for algae cultivation, and also generate biogas and/or bio-electricity as alternative energy. Pretreater 408 is capable of generating an effluent/wastewater stream 806 with reduced odor and biochemical oxygen demand (BOD), which is advantageous for water quality. However, typically the pretreatment process of pretreater 408 does not remove nitrogen and phosphorus, which is a significant environmental issue, and due to government regulations typically requires further treatment for its safe discharge into natural water bodies. SAS 400 recovers the nutrients from effluent/wastewater via algae cultivator 412, which can be, for example, an embodiment of algal growth system 108 as described herein or as a standalone growth system or as a combination of an algal growth system supporting photoautotrophic, mixotrophic, or heterotrophic mode of production of algae utilizing appropriate algae strains.

At a desired time, the algal biomass produced by algae cultivator 412 is harvested at biomass harvester 416, which outputs lipids, water, and solids—each of which can be a useful produce or recycled within SAS 400. For example, lipids are extracted at oil extractor 420; water can be recycled into one or more of the other processes within SAS 400 such as algae cultivator 412 or back to one of the stakeholders (such as a dairy farm); and solids can be converted into animal feeds or fertilizers. The post-harvest algal biomass (also referred to as algae cake), and/or other algal biomass is utilized for production of additional useful byproducts, such as fertilizer or animal feed depending on the throughput feedstock used. For example, algae biomass grown with dairy manure waste would be more appropriate as a fertilizer instead of animal feed due to required FDA compliance. In contrast, brewery effluent, which is a cleaner byproduct of beer processing and typically being food grade, can be used for producing algal biomass for high value animal feed. The crude oil extracted by oil extractor 420 goes through further processing to obtain desirable end products (biodiesel, oil-heat, jet fuel), and is then stored, transported and used in vehicles, planes or for heating purposes. Notably, as algae is a CO2 sink, one can expect that at least a portion of the CO2 generated by the local use of the aforementioned products can be recaptured by the algal biomass production process along with the CO2 from the farm operations. Heat captured by pretreater 408 or from other onsite operations can be used as a heat input for algae cultivator 412, biomass harvester 416, oil extractor 420, and/or for sterilizing the algae cake that is used for animal feed production. Solid separator 804 separates the solids produced by pretreater 408 and can be used for production of fertilizer or soil mixes or soil amendments for plant growth described below in the exemplary compositions, Solid separator 804 can include a drying component (not shown). Solids separating can be accomplished by screening, using a centrifuge, or via other technologies known in the art.

Certain compositions discussed herein use digestate solids (which is a byproduct of anaerobic digestors that contains things, such as, fibrous undigested organic material made of lignin and cellulose, some microbial biomass, animal hair, and nitrogen, phosphorus and other nutrients) produced by most any type of anaerobic digester such as, but not limited to, covered storage, plug flow digester, mixed plug flow digester, complete mix digester, fixed film digester, induced blanket digester, two-stage digester etc. Notably, the digestate solids are almost pathogen free.

In an embodiment, SAS 800 can include enhanced biological phosphorus removal system 808 that uses the naturally occurring microorganisms present in the waste stream. Removal system 808 may consist of alternating anaerobic (absence of oxygen) and aerobic conditions. In this situation, in the anaerobic phase, phosphorus accumulating organisms (PAOs) are used for the biological processing of slurry/sludge/effluent obtained through for example, anaerobic digestion. In operation, the PAOs consume the volatile fatty acids, such as acetate, in the slurry/sludge/effluent, which is further converted into poly-$\beta$-hydroxyalanoates (PHA). In the follow up aerobic phase the PAOs grow and consume more phosphorus as a result of accumulation of polyphosphate within their cells. This predominantly bacterial biomass is separated through one or more processes of solid concentration and separation described herein (e.g., via solids separator 804). The separated biomass can, as explained elsewhere herein be pretreated for removal of the effect of pathogens, moisture content and/or pH adjusted and used as a component of fertilizer or soil mix composition. In certain embodiments removal system 808 can be an add on feature to an SAS or in some situations can replace solids separator 804.

Notably, PAOs and algae (photoautotrophic, and/or mixotrophic and/or heterotrophic) can be grown together in anaerobic and/or aerobic phases described above with the appropriate algae strains.

Removal system 808 can include flocculation, where polymer or coagulant chemicals or binders are added including one or more of organic polymers, inorganic polymers—polyacrylamides, chemicals, FeCl2, FeSO4, AlSO4 etc.

In an embodiment of removal system 808, the enhanced biological phosphorus removal system is followed by struvite crystallization for maximizing the nutrient recovery (discussed further below with respect to FIG. 12, below).

Generally, after solids separation, the slurry/sludge/effluent is treated with chemicals including magnesium chloride in an amount sufficient to combine with ammonia and phosphorus in an approximately in a mole to mole to mole ratio (1:1:1) of magnesium, ammonia and phosphate so as to crystallize as Magnesium-Ammonium-Phosphate (MAP) or struvite ($MgNH_4PO_4.6H_2O$), which is then separated and washed.

Figure 11:
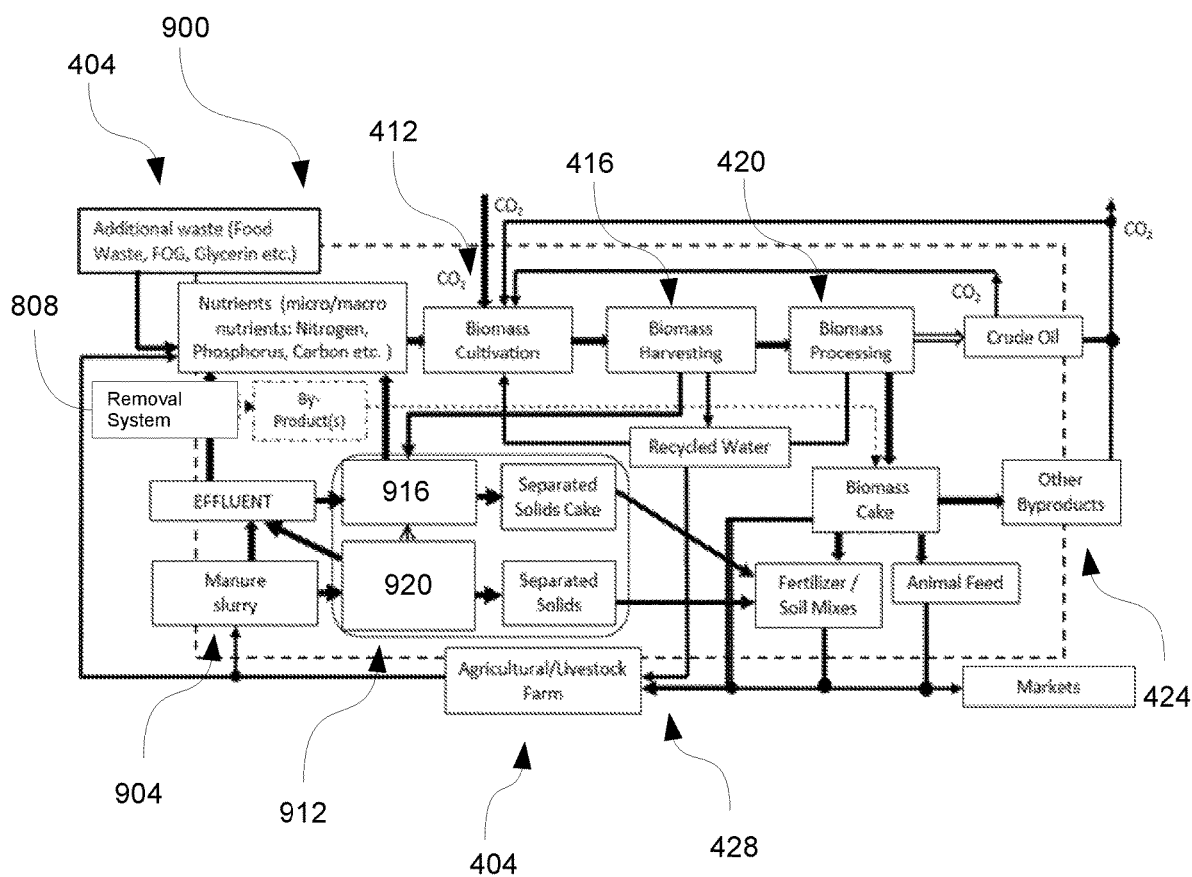
FIG. 11 is a block diagram of an exemplary symbiotic algae system according to yet another embodiment of the present invention.

Turning to FIG. 11, there is shown another exemplary SAS, SAS 900, which, in contrast to other SAS systems discussed herein, receives nutrients from a slurry collection system 904. Slurry collection system 904 can be an open or a closed structure or container to contain the waste slurry or sludge that optionally facilitates aeration and/or recirculation and/or flocculation of slurry/sludge.

Additionally, SAS 900 can receive one or all of the nutrients from the effluent generated by an additional nutrient recovery process 908 that treats the slurry from slurry collection system 904 so as to recover nutrients such as phosphorus and/or nitrogen in a range from about 0.5% to about 99% depending on the concentration of nutrients in the slurry/sludge or effluent processed through a solids separator 912, which in this exemplary embodiment includes a processing centrifuge 916 and a screw press composter 920 to produce a separator solids cake and a separated solids, respectively. The pH of the slurry/sludge or effluent is optionally adjusted by the use of acidic or basic additives.

Screw press composter 920 generates the two streams—a liquid and a solid. The solid portion goes through further processing through a composter (not shown) such as drum composter, and the solids are separated. The liquid portion goes through a solid concentration or separation process through screening and/or an equipment such as a centrifuge to separate the solids with higher concentration of nitrogen and or phosphorus compared to the first iteration of solid separation through an equipment such as a screw press. In an exemplary process processing centrifuge 916 directly receives inputs from slurry collection system 904. The effluent generated become additional feed stock inputs 404. The digestate solids and/or the separated solid cake produced slurry collection system 904 are optionally processed or sterilized to make a pathogen free material usable for production of fertilizer or soil mixes or soil amendments for plant growth described below in the exemplary compositions.

Figure 12:
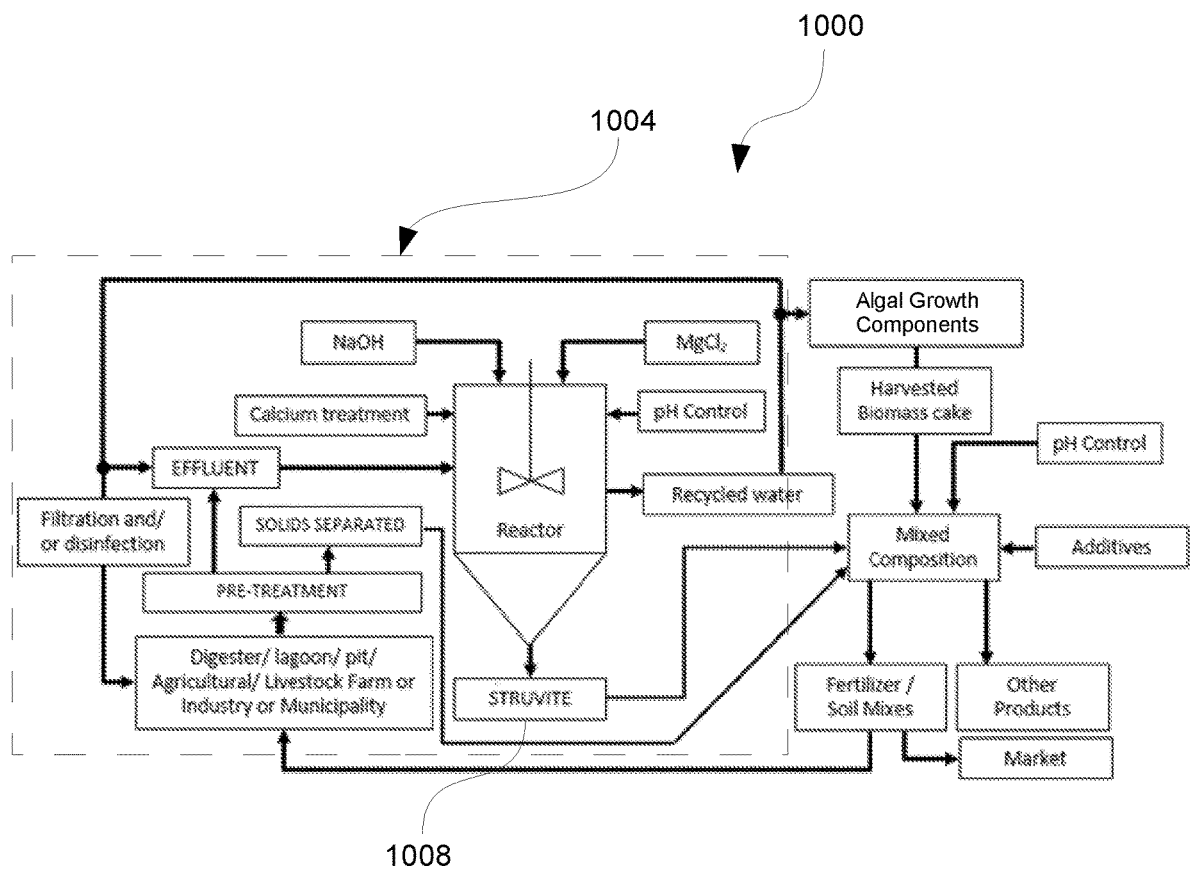
FIG. 12 is a block diagram of a portion of an exemplary symbiotic biomass production system integrated with struvite crystallization system according to an embodiment of the present invention.

Turning now to FIG. 12, which shows a SAS 1000 including a removal system 1004 that includes struvite crystallization 1008. In operation, the pH is adjusted to form the MAP crystals. Crystallized struvite appears is sparingly soluble in neutral and alkaline conditions, but readily soluble in acid. MAP is used as one of the components of fertilizer or the soil mixes described below. In some cases, depending on the types of slurry/sludge and/or effluent (such as dairy manure containing calcium-phosphate), precipitates are run through acidic pretreatment for releasing the phosphorus contained in the precipitates, which is then treated with magnesium chloride that crystallizes as MAP (as discussed above). The acid pretreatment of calcium to release phosphorus can optionally involve lowering pH or addition of acids. One of the benefits of separating MAP prior to feeding the nutrients to a biomass system, such as a SAS, is that it reduces the inefficiency within the biomass/algal growth and harvest system because of clogging of the plumbing, pipes, pumps and other equipment caused by excessive phosphorous. Another benefit of the recovered struvite or the crystallized phosphorus is that it can be mixed with algae and/or separated solids and/or other components to make fertilizer or soil mixes. For example, standalone struvite fertilizer has a low nitrogen, high phosphorus N—P—K value, e.g., 6:29:0. However, issues with using standalone struvite as fertilizer can include an increase in soil pH level that may affect the nutrient uptake by plants and plants cannot intake all of the magnesium component. In contrast, combining struvite with biomass based fertilizer and adding additives to balance N—P—K and/or pH makes the nutrients better available for plants.

Figure 13:
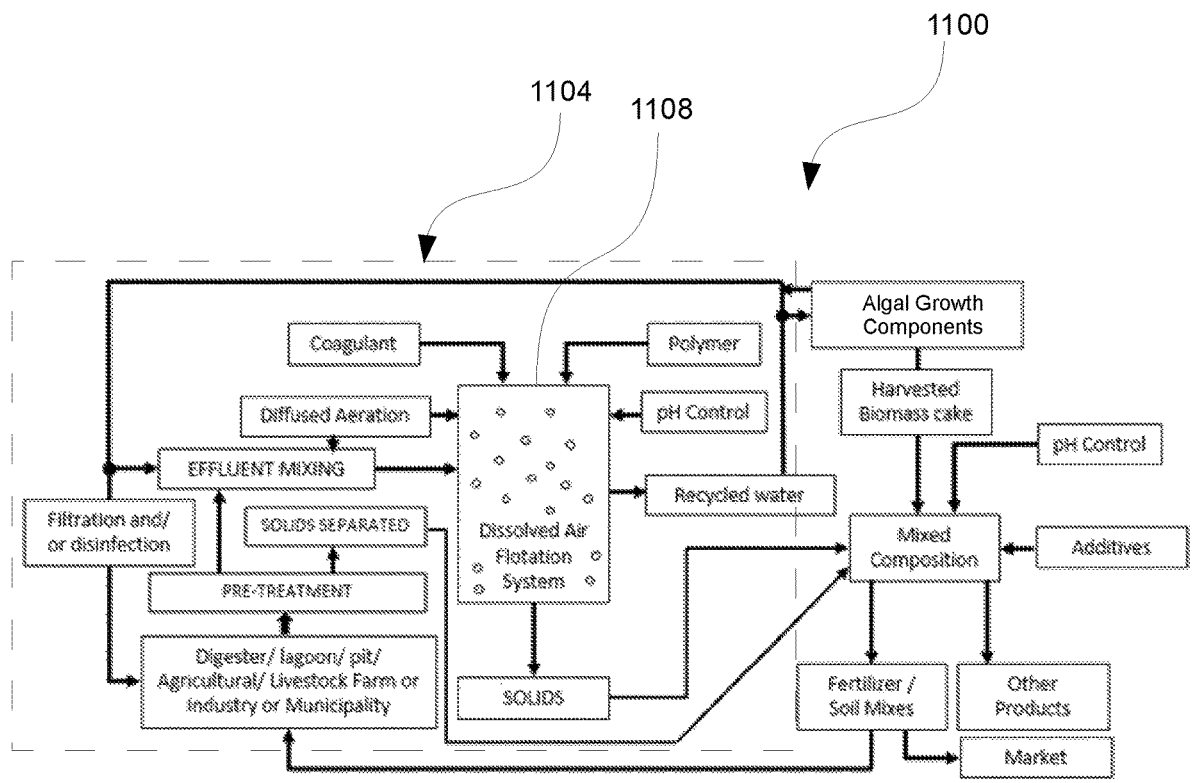
FIG. 13 a block diagram of a portion of an exemplary symbiotic biomass production system integrated with a dissolved air floatation system according to an embodiment of the present invention.

In another embodiment, and as shown in FIG. 13, a SAS 1100 includes a removal system 1104 that has a dissolved air flotation (DAF) system 1108 that is downstream of a solids separator 1112. In this embodiment of DAF system 1108, compressed air is passed through water to form bubbles from dissolved air, and then mixed with the screened slurry/sludgy/effluent so that the bubbles adhere to the suspended solids to push those to the surface, where they are separated through flocculation. Typically, pH adjustment is then done. Pretreatment through the use of flocculants (described earlier) is done to improve the suspended solids removal. The solids, containing elements such as phosphorus, are separated through mechanical means such as an auger screw press, filter press, belt filter press, centrifuge etc. The effluent generated is fed to a SAS, such as SAS 400. The separated solids can be used as a component in the fertilizer or soil mixes. In certain embodiments of SAS 1100, an ammonia-stripper may be used to adjust pH and temperature before water is passed through it for stripping ammonia.

Any of the systems described herein can include filtration and/or disinfection systems Screening can be sequential, mechanical, chemical or both, so as to separate the solids that can interfere in the biomass growing process. Disinfection of nutrient containing effluent or aqueous material used for biomass growth or the biomass itself can be completed using steam and/or chemical treatment and/or ultraviolet treatment to make the biomass pathogen free. Exemplary algal strains include, but are not limited to, *Chlorella vulgaris, Chlorella pyrenoidosa, Spirulina platensis, Haematococcus pluvialis, Athrospira* sp. *Scenedesmus* sp., and other algae strains such as Dunalliella rich in Highly Unsaturated Fatty Acids for aquaculture.

The disclosed composition(s) below can be used as nutrients or fertilizers or soil mixes for plant growth in farming operations, in open or closed or partially covered crop fields, greenhouses, hoop houses, or low tunnel based plant growth operations, private gardens, yards, floriculture, aquaponics, or hydroponics. Some of the compositions enhance soil aeration and provide peat-moss amendments with high water retention capabilities.

Exemplary Valued Products

Some of the compositions are 'organic' and/or 'biobased' and/or 'biopreferred' where compositions of N—P—K provide 75% (or above) organic carbon-based nutrition for plant growth. Some of these compositions contain one or more components from the waste grown biomass, and/or one of more byproducts of processes described herein, such as separated solids, phosphorus cake or crystals etc. and/or the additives described herein. The composition is pH balanced.

An exemplary embodiment of a composition for plant growth and/or soil fertility is comprised of dry weight N—P—K percentages of around 1.42-1.40-1.37, respectively (equivalent to N—P—K 1-1-1 percentages). The disclosed exemplary composition is made from:

a) predominantly suspended microalgae biomass grown with the liquid effluent from anaerobically digested manure and/or co-digested with food waste;
b) ash and/or biochar from organic source—a byproduct of burning wood;
c) digestate solids produced as byproducts of co-digestion; and
d) pH adjustment using an additive.

Another exemplary composition comprises 1.97-1.86-1.3 N—P—K percentages equivalent to 2-2-1. The composition is made from:
a) predominantly suspended microalgae biomass grown with the liquid effluent from anaerobically digested manure and/or co-digested with food waste;
b) Ash and/or biochar from organic source a byproduct of burning wood; and
c) pH adjustment using an additive.

An exemplary composition suitable as a potting mix capable of retaining moisture between 1.5 to 5 times its dry weight includes N—P—K about 0.85-0.40-0.12 having a 5:95 composition of:
a) predominantly biomass (e.g. suspended microalgae) grown with the liquid effluent from anaerobically digested manure and/or co-digested with food waste, and/or effluent from solid separation and/or pretreatment;
b) separated solids produced; and
c) pH adjustment using an additive.

An exemplary composition suitable for use as a potting mix contains a combination of:
a) predominantly suspended microalgae 1 biomass grown with the liquid effluent from anaerobically digested manure and/or co-digested with food waste;
b) separated solids produced as byproducts of digested manure and/or co-digested with <5% food waste;
c) Peat moss, coir, vermiculite to reduce the existing use of peat moss, and vermiculite without depriving the soils of benefits from these, whereas provide an alternative to reduced use of peat moss and vermiculite; and
d) pH adjustment.

Another exemplary composition of fertilizer mix contains enriched nitrogen content and is formed from:
Biomass (e.g. predominantly suspended microalgae) grown with the liquid effluent from anaerobically digested manure and/or co-digested with food waste;
b)) nutrient enhancement material(s) that may be a byproduct of a process and/or a fertilizer available, such as, but not limited to one or more of: Ammonium Nitrate (NH4NO3) [grade: 37-0-0, composition: 18.5% N—NO3 (Nitrate nitrogen), 18.5% N—NH4 (Ammonium nitrogen)]; Ammonium Sulfate ((NH4)2SO4) [grade: 21-0-0, composition: 21% N—NH4, (Ammonium Nitrogen) 73% SO4 (sulfate)]; Ammonium Sulfate Nitrate (H12N4O7S) [Grade: 26-0-0, composition: 19% N—NH4 (Ammonium nitrogen), 7% N—NO3 (Nitrate nitrogen), 14.5% S—SO4 (Sulfate)]; Calcium Ammonium Nitrate (5Ca(NO3)2-NH4NO3*10H2O) [grade: 15.5-0-0, composition: 14.4% N—NO3, 1.1% N—NH4, 19% Ca]; Magnesium Nitrate (Mg(NO3)2) [grade: 11-0-0 0-9.6; composition: 11% N—NO3, 9.6% Mg]; Magnesium Sulfate (MgSO4) [grade: 0-0-0-0-9.1; composition: 9.1% Mg, 14% S (42% SO4)]; Mono Ammonium Phosphate (MAP) (NH4H2PO4) [grade: 12-61-0, composition: 12% N—NH4, 26.5% P (61% P2O5)]; Mono Potassium Phosphate (MKP) (KH2PO4) [grade: 0-52-34, composition: 22.5% P (52% P2O5), 28% K (34% K2O)]; Potassium Nitrate (KNO3) [grade: 13-0-46, composition: 13% N—NO3, 38% K (46% K2O)]; Potassium Sulfate (K2SO4) [grade: 0-0-52, composition: 43% K (52% K2O), 18% S (54% SO4)]; Urea. CO(NH2)2 [grade: 46-0-0, composition: 46% N—NH2]; Potassium Chloride (KCl) [grade: 0-0-60, composition: 50% K (61% K2O)]; Copper Sulfate (CuSO4*5H2O) [composition: 25% Cu, 13% S]; Zinc Sulfate (ZnSO4*7H2O) [composition: 22% Zn, 11% S]. In an instance of bio-preferred composition includes the standard allowed limit such as at least 75% organic material and the amount of enhancement nutrient is added accordingly; and
c) Additives and/or pH adjustment and/or organic solids.

An exemplary composition of fertilizer contains a combination of:
a) predominantly suspended microalgae biomass grown with the liquid effluent from anaerobically digested manure and/or co-digested with <5% food waste Separated solids produced as byproducts of livestock manure or co-digestion;
b) struvite; and
c) pH adjustment.

The fertilizer compositions described above can be a slow release fertilizer (also known as controlled release or extended release), in which the composition includes the slow release enhancing ingredients and/or coating on the granules. Alternatively, a "reactive layer coating" can be made by applying reactive monomers to the soluble grains or particles of the fertilizer.

In an exemplary embodiment, the biomass produced by the SAS' described herein is from the aquatic species suitable for growing animal feed or for nutraceuticals. For example:
a) 15% Predominantly *Spirulina platensis* biomass (over 50% crude protein content) grown using the strain with the pretreated liquid effluent from anaerobically digested manure and/or co-digested with <5% food waste;
b) 85% ordinary daily ration including grains/meal (from soybean, corn etc. for high energy and starch content), hay forages, alfalfa etc; and
c) Supplements.

Additional Examples

The following examples are provided to illustrate certain embodiments and are not to be construed as limitations on the embodiments, as set forth in the claims. All parts and percentages are by weight unless otherwise specified.

Example 1

An organic and/or biobased and/or biopreferred fertilizer composition with a moisture content 4% or less comprised of following:
a) over 75% predominantly algal biomass grown with the liquid effluent from anaerobically co-digested manure with <5% food waste;
b) ash for enhancing potassium concentration;
c) soybean meal for enhancing nitrogen content; and
d) pH adjustment via an additive option.

Example 2

A set of tests were conducted to determine growth of vegetable (lettuce) in a controlled greenhouse environment. The market brand soil mix was used that contained 75-85%

Sphagnum peat moss, perlite (horticultural grade), vermiculite (horticultural grade), dolomite and calcitic limestone (pH adjuster), wetting agent, mycorrhizae—endomycorrhizal fungi (*Glomus intraradices*) as one active propagule per gram of growing medium. The 25%, 50% and 100% fertilizer composition was mixed with the soil mix in the respective batches of trials. All the pots were watered with measured amounts of water sufficient to retain the moisture and not flow out. The control had no fertilizer. In each pot 5 seeds of lettuce were sown. After the seedling germinated and first leaves emerged, the plants were thinned to two plants.

Figure 14A:
FIGS. 14A-D are photographs of exemplary plants provided certain amounts of nutrients produced by a symbiotic algae system according to an embodiment of the present invention.
Figure 14C:
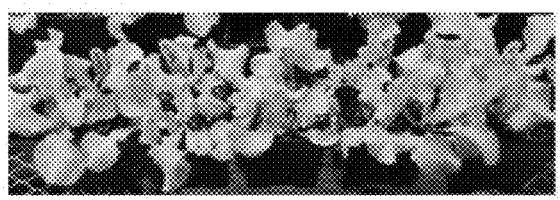
Figure 14B:
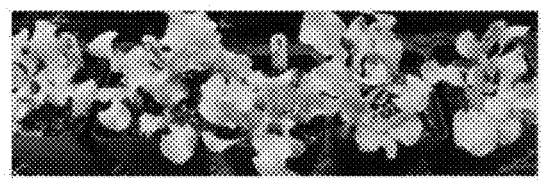
Figure 14D:
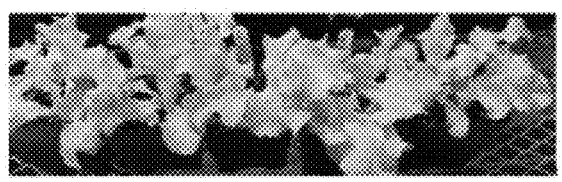

As shown in FIG. 14:
a) FIG. 14A: control with no added fertilizer;
b) FIG. 14B: 25% fertilizer composition;
c) FIG. 14C: 50% fertilizer composition; and
d) FIG. 14D: 100% fertilizer composition.

There was a significant effect of fertilizer composition on the shoot biomass. All the three compositions resulted in increases in shoot growth, with the highest being the 100% composition.

Figure 15:
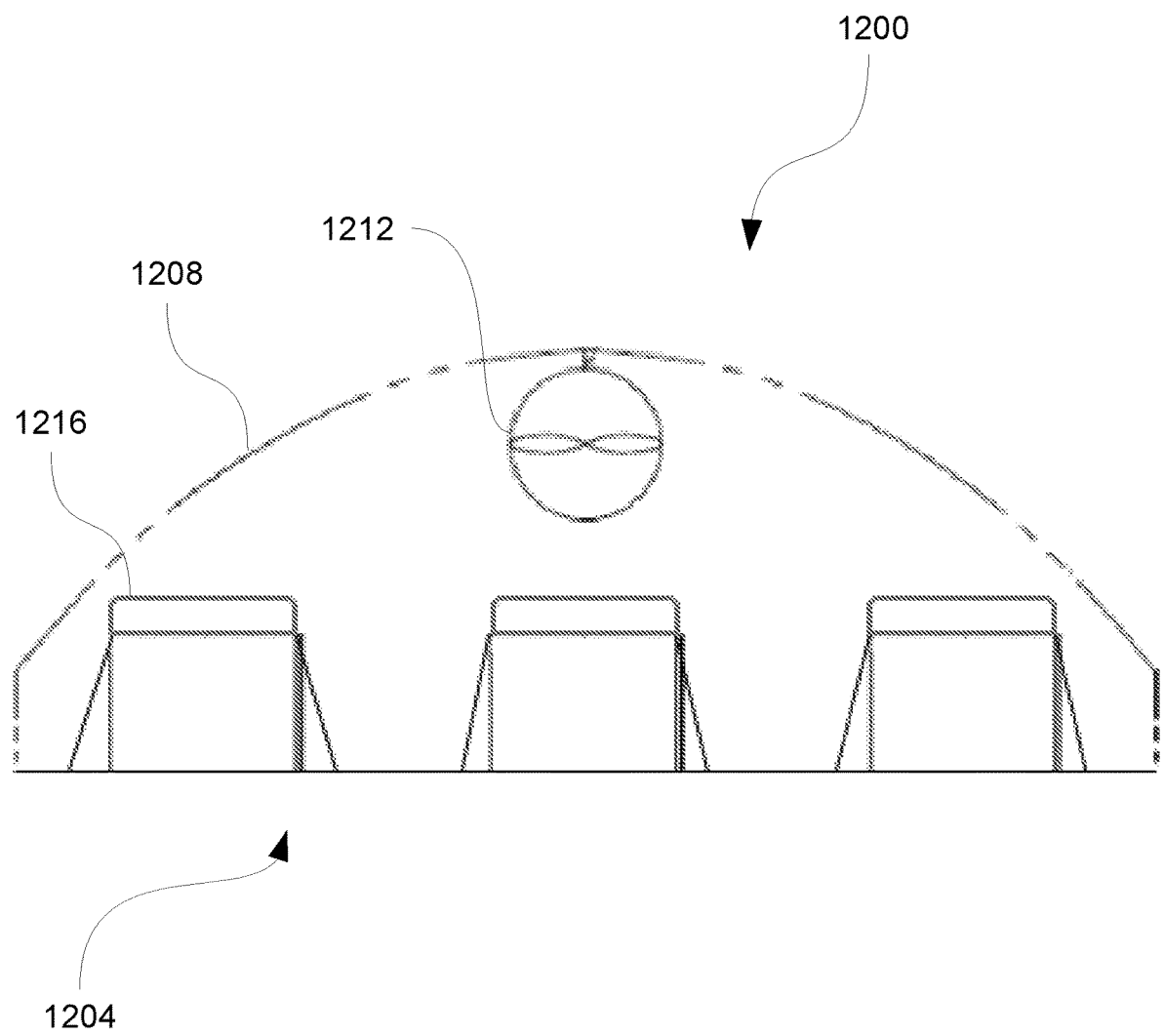
FIG. 15 is a schematic diagram of an exemplary canal structure suitable for growing algae according to an embodiment of the present invention.

FIG. 15 shows an exemplary growth structure 1200 for use with an algae growth system as described herein. In this embodiment, growth structure 1200 includes a plurality of raised canals 1204, a covering 1208, an aeration component 1212, and a canal cover 1216. Each canal can be a three-sided container that has sides made of light-penetrating materials to allow for certain types of algal growth. As shown, canals 1204 are located inside a covering 1208 that is also made from light-penetrating materials. Light-penetrating materials can be, but is not limited to, plastic, polyethylene, polystyrene, acrylic, acetal, and fiberglass. In alternative embodiments, each canal can be either entirely or partially covered by canal cover 1216, which is also typically made from light-penetrating materials. Overall, growth structure 1200 can be a small as a few square feet to as large as 100,000 acres. Each canal 1204 can be as long and wide and high as desired. Although three canals are shown in FIG. 15, the number of canals may vary as desired.

In an exemplary aspect, a symbiotic algae system is disclosed that comprises: a first algal growth component, wherein the first algal growth component includes a heterotrophic organism, and wherein the first algal growth component produces a first effluent and an off-gas; and a second algal growth component is fluidly coupled to the first algal growth component, and the second algal growth component including at least one organism from the group of: a photoautotrophic organism, a mixotrophic organism, and a heterotrophic organism, and wherein the second algal growth component receives, as an input, the first effluent and the off-gas and produces a second effluent. In the symbiotic algae system, the first algal growth component can receive, as a first input, an effluent input or a waste input. In the symbiotic algae system, the second algal growth component can receive, as a second input, an effluent input or a waste input. The symbiotic algae system can further include a waste nutrient preparation sub-system fluidly coupled to the first algal growth component. In the symbiotic algae system, the waste nutrient preparation sub-system can receive an effluent input, a fresh water input, and waste input, and outputs an effluent suitable for use by the first algal growth component. In the symbiotic algae system, the waste nutrient preparation sub-system is a manure settling and solid's preparation unit that outputs liquid manure waste to the first algal growth component. The symbiotic algae system can further include an algal harvesting system having at least one separator, wherein the algal harvesting system is fluidly coupled to the first algal growth component and/or the second algal growth component. The symbiotic algae system can have an EROI greater than 10. The symbiotic algae system can have an EROI of about 40. The symbiotic algae system can further comprise a third algal growth component, wherein the third algal growth component includes at least one organism from the group of: a photoautotrophic organism, a mixotrophic organism, and a heterotrophic organism, and wherein the third algal growth component receives, as an input, the second effluent. The symbiotic algae system can further comprise at least one biomass processing unit, the biomass processing unit sized and configured to extract lipids from at least one of the first algal growth component and the second algal growth component.

In another exemplary aspect, a symbiotic algae system is disclosed that comprises a first algal growth component, wherein the first algal growth component includes a heterotrophic organism, and wherein the first algal growth component produces an first effluent and an off-gas; and a second algal growth component fluidly coupled to the first algal growth component, wherein the second algal growth component includes at least one organism from the group of: a photoautotrophic organism, a mixotrophic organism, and a heterotrophic organism, and wherein the second algal growth component receives, as a first input, the first effluent and the first off-gas and produces an second effluent and a second off-gas; and wherein the second effluent and the second off-gas are received as inputs to the first algal growth component. In the symbiotic algae system, the first algal growth component can receive, as an additional input, an effluent input or a waste input, and wherein the additional input and the second effluent include a nitrogen and a phosphorous. In the symbiotic algae system, the first algal component can removes a portion of the nitrogen and the phosphorous from the second input and the additional input. The symbiotic algae system can further comprise a third algal growth component, wherein the third algal growth component includes at least one organism from the group of: a photoautotrophic organism, a mixotrophic organism, and a heterotrophic organism, and wherein the third algal growth component receives a portion of the second effluent. The symbiotic algae system can further comprise at least one biomass processing unit, the biomass processing unit sized and configured to extract lipid/oil from at least one of the first algal growth component and the second algal growth component. The symbiotic algae system can have an EROI greater than 10 The symbiotic algae system can have an EROI of about 40.

In yet another exemplary aspect, a symbiotic algae system can comprise: a waste nutrient preparation sub-system; an algal culturing system including: a first algal growth component fluidly coupled to said waste-nutrient preparation sub-system, wherein the first algal growth component includes a heterotrophic organism, and wherein the first algal growth component produces a first effluent and an off-gas; and a second algal growth component, wherein the second algal growth component includes at least one organism from the group of: a photoautotrophic organism, a mixotrophic organism, and a heterotrophic organism, and wherein the second algal growth component receives, as an input, the effluent and the off-gas and produces a second effluent; and an algal harvesting system fluidly coupled to said algal culturing system; an algal biomass processing system fluidly coupled to said algal harvesting system; and a byproducts system fluidly coupled to said algal biomass processing system. In the symbiotic algae system, the waste nutrient preparation sub-system can receive, as an input, an effluent input or a waste input.

Additives for composition adjustment and/or enhancement and/or pH control/adjustment by using one or more or a combination of following: granular, hydrated, pelletized, pulverized, solid, liquid, gel, emulsion, dispersion, suspended, dissolved, water soluble, water insoluble, powder, byproducts or other forms of following, but not limited to: limestone or lime (such as calcitic limestone—mostly calcium carbonate, and dolomitic limestone to mostly add magnesium); potash such as potassium chloride, potassium sulfate, potassium carbonate, or potassium nitrate etc.; wood ash; ash from other sources, such as plants, ligno-cellulosic material; lignoSulphonate oils; biochar; coal, sulfur; sulphates, carbonates; phosphates (may be one or more of organophosphate, an ester of phosphoric acid, and/or inorganic chemical(s) and a salt-forming anion of phosphoric acid); orthophosphate and polyphosphate, pyrophosphate, hydrogen phosphates; dihydrogen phosphates; rock phosphate, treated or untreated fluorapatite $Ca_5(PO_4)_3F$ (CFA) and/or hydroxyapatite $Ca_5(PO_4)_3OH$; organic and inorganic forms of nitrogen (such as soybean or cottonseed meal), nitrogen fertilizer (nitrogen as urea, ammonium, nitrate or a mix); liquid nitrogen, calcium nitrate, anhydrous ammonia, ammonia, ammonium nitrate; straight fertilizers; struvite (magnesium ammonium phosphate) $NH_4MgPO_4.6H_2O$; Isobutylidenediurea (IBDU)—a single compound with the formula $(CH_3)_2CHCH(NHC(O)NH_2)_2$ whereas the urea-formaldehydes consist of mixtures of the approximate formula $(HOCH_2NHC(O)NH)_nCH_2$, animal wastes, plant wastes from forest or agriculture, and treated sewage sludge or biosolids, livestock manure(s), products from the slaughter of animals including blood meal, bone meal, feather meal, hides, hoofs, horn etc.; oxalates; aluminum sulfate, iron sulfate; fertilizer (acidifying/alkalizing, containing ammonia—such as ammonium nitrate, urea, or amino acids); peat moss, sphagnum peat; rare earth(s); clays; mud; soil; silicates; organic or inorganic deposits of biological matter; diatom; other organic or inorganic acidic or basic material; ligno-cellulosic material or waste, molasses, starch, pitch, surfactants, oil, hydrocarbons; pesticides, insecticides, herbicides, fungicides and plant growth regulators, solvent, solution, wax, polymers, binders, organic or inorganic minerals, tar, asphalt, buffering agent, oxidizing agent (chlorine, chlorine dioxide, hydrogen peroxide, acid, permanganates, sulfur dioxide, phenols, alcohols, oxyanions etc.), reducing agent (e.g. thiosulphate), anti-caking agent (e.g. magnesium hydrooxide), conditioner, glycerin, glyceride, existing product(s) in market, use of energy or rays (thermal, ultraviolet light, ultrasonic, electromagnetic, gamma etc.), pressure balance etc.; materials for controlled release or fertilizers encapsulation in a shell for degradation at a specified rate, such as Sulfur, thermoplastics, ethylene-vinyl acetate, surfactants, etc. to produce diffusion-controlled release of nutrients. "Reactive Layer Coating" for reactive monomers, fatty acid salts, paraffin, topcoat material(s). The pH control for the degree of acidity and alkalinity is measured on a scale of 0-14, with a pH of 7 is neutral, 0 to 7 is acidic, and 7 to 14 is alkaline. For example, the ideal soil pH for vegetables and lawn grasses is 6.5, just a little on the acidic side.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A process for preparing a fertilizer, food, or oil product from a waste stream comprising:
    selecting an algae strain based upon whether the waste stream is nitrogen rich or phosphorus rich;
    growing an algal biomass from the algae strain, using portions of the waste stream as a feedstock;
    extracting a solids portion from the algal biomass; and
    preparing the fertilizer, food, or oil product from the solids portion,
    wherein the growing the algal biomass is completed in a symbiotic algae system and includes:
        growing the algae strain in a first container, wherein the algae strain is a heterotrophic algal growth strain, wherein the algae strain produces carbon dioxide and byproducts, and wherein the algae strain is grown in the first container without exposure to light; and
        growing a second algae strain in a second container, wherein the second algae strain is photoautotrophic, wherein the carbon dioxide and byproducts from the first container are supplied to the second container, and wherein the second container is exposed to light.

2. The process according to claim 1, further including the step of pretreating the waste stream using anaerobic digestion in an anaerobic digester.

3. The process according to claim 1, wherein the algae strain is chosen so as to remove either primarily nitrogen or primarily phosphorus.

4. The process according to claim 1, further including removing a portion of a phosphorus component from the waste stream prior to growing the algal biomass.

5. The process according to claim 1, further including:
    mixing an ash and/or biochar into the first container; and
    adjusting the pH of a fluid in the first container with an additive.

6. The process according to claim 1, wherein the second algal strain produces oxygen and wherein the oxygen is fed from the second container to the first container.

7. The process according to claim 1, further including a pretreater for pretreating the waste stream.

8. The process according to claim 7, wherein the pretreater is selected from the group consisting of:
    an anaerobic digester, a phosphorus removal system, a struvite crystallization system, a dissolved air floatation system, a nitrogen removal system, an ammonia stripping system, a combination of phosphorus and nitrogen removal system; a phosphorus removal system alternates between anaerobic and aerobic conditions, a pyrolysis system, a phosphorus removal system that includes a bacterium, and a phosphorus removal system that includes a flocculation stage.

9. The process according to claim 8, wherein the pretreater also produces a solid waste and a solids component.

10. The process according to claim 1, further including an algal harvesting system having at least one separator, wherein the algal harvesting system is fluidly coupled to the first container and the second container.

11. The process according to claim 1, further including separating an effluent component of the waste stream from a solid waste component of the waste stream.

12. The process according to claim 1, wherein the algal biomass is grown in a canal structure made from light-penetrating materials.

13. The process according to claim 1, further including separating solids from the waste stream.

* * * * *